US008428910B2

(12) United States Patent
Papadimitriou et al.

(10) Patent No.: US 8,428,910 B2
(45) Date of Patent: *Apr. 23, 2013

(54) AUTONOMOUS FITNESS FOR SERVICE ASSESSMENT

(76) Inventors: Wanda G. Papadimitriou, Houston, TX (US); Stylianos Papadimitriou, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/304,061

(22) Filed: Nov. 23, 2011

(65) Prior Publication Data

US 2012/0130651 A1     May 24, 2012

Related U.S. Application Data

(60) Continuation-in-part of application No. 10/867,004, filed on Jun. 14, 2004, now Pat. No. 7,240,010, and a continuation-in-part of application No. 10/995,692, filed on Nov. 22, 2004, now Pat. No. 7,155,369, and a continuation-in-part of application No. 11/079,745, filed on Mar. 14, 2005, now Pat. No. 7,231,320, and a continuation-in-part of application No. 11/743,550, filed on May 2, 2007, now Pat. No. 7,403,871, and a continuation-in-part of application No. 11/769,216, filed on Jun. 27, 2007, now Pat. No. 8,086,425, and a continuation-in-part of application No. 11/772,357, filed on Jul. 2, 2007, now Pat. No. 8,050,874, and a division of application No. 11/769,216, filed on Jun. 27, 2007, now Pat. No. 8,086,425.

(51) Int. Cl.
*G01N 29/00* (2006.01)

(52) U.S. Cl.
USPC ............................ 702/185; 702/183; 704/272

(58) Field of Classification Search .................... 73/1.82, 73/53.06; 702/183, 185; 704/272
See application file for complete search history.

(56) References Cited

U.S. PATENT DOCUMENTS

| | | | |
|---|---|---|---|
| 1,823,810 | A | 9/1931 | Wall |
| 2,194,229 | A | 3/1940 | Johnston et al. |
| 2,317,721 | A | 4/1943 | Barnes |
| 2,527,000 | A | 10/1950 | Drake |
| 2,582,437 | A | 1/1952 | Jezeweski et al. |
| 2,685,672 | A | 1/1954 | Price et al. |
| 2,770,773 | A | 11/1956 | Cooley |
| 2,881,386 | A | 4/1959 | Price et al. |
| 2,927,321 | A | 3/1960 | Harris |
| 3,202,914 | A | 8/1965 | Deem et al. |
| 3,225,293 | A | 12/1965 | Wood et al. |
| 3,238,448 | A | 3/1966 | Wood et al. |
| 4,523,468 | A | 6/1985 | Derkacs et al. |
| 4,629,985 | A | 12/1986 | Papadimitriou et al. |
| 4,698,631 | A | 10/1987 | Kelly, Jr. et al. |

(Continued)

OTHER PUBLICATIONS

Papadimitriou, Steve et al, "The Inspection of Used Coil Tubing", Second International Conference and Exhibition on Coiled Tubing Technology, Adams Mark Hotel, Houston, Texas, Mar. 28-31, 1994.

*Primary Examiner* — Daniel D Abebe
(74) *Attorney, Agent, or Firm* — Kenneth L. Nash

(57) ABSTRACT

The equipment comprises at least one computer and a material features acquisition system operable to detect a plurality of material features. The features are then evaluated according to rules that capture the multidiscipline knowledge of experts and are already inputted into the computer. The computer iterations are processed until an acceptable conclusion is made regarding the condition of the material under evaluation.

51 Claims, 19 Drawing Sheets

U.S. PATENT DOCUMENTS

| | | | |
|---|---|---|---|
| 4,710,712 A | 12/1987 | Bradfield et al. | |
| 4,821,575 A | 4/1989 | Fujikake et al. | |
| 4,825,385 A | 4/1989 | Dolph et al. | |
| 5,202,680 A | 4/1993 | Savage | |
| 5,210,704 A | 5/1993 | Husselny | |
| 5,321,362 A | 6/1994 | Fischer et al. | |
| 5,371,462 A | 12/1994 | Hedengren et al. | |
| 5,430,376 A | 7/1995 | Vierti | |
| 5,440,237 A | 8/1995 | Brown et al. | |
| 5,455,777 A | 10/1995 | Fujiyama et al. | |
| 5,621,172 A * | 4/1997 | Wilson et al. | 73/579 |
| 5,648,613 A | 7/1997 | Kiefer | |
| 5,671,155 A | 9/1997 | Edens et al. | |
| 5,774,378 A | 6/1998 | Yang | |
| 5,777,891 A | 7/1998 | Pagano et al. | |
| 5,786,768 A | 7/1998 | Chan et al. | |
| 5,914,596 A | 6/1999 | Weinbaum | |
| 5,943,632 A | 8/1999 | Edens et al. | |
| 5,970,438 A | 10/1999 | Clark et al. | |
| 6,115,674 A | 9/2000 | Brudnoy et al. | |
| 6,279,125 B1 | 8/2001 | Klein | |
| 6,359,434 B1 | 3/2002 | Winslow et al. | |
| 6,378,387 B1 | 4/2002 | Froom | |
| 6,480,811 B2 | 11/2002 | Denny et al. | |
| 6,560,555 B1 | 5/2003 | Mallory | |
| 6,580,268 B2 | 6/2003 | Wolodko | |
| 6,594,591 B2 | 7/2003 | Clark et al. | |
| 6,697,466 B2 | 2/2004 | Howard et al. | |
| 6,727,691 B2 | 4/2004 | Goldfine et al. | |
| 6,784,662 B2 | 8/2004 | Schlicker et al. | |
| 6,836,560 B2 | 12/2004 | Emery | |
| 6,847,207 B1 | 1/2005 | Veach et al. | |
| 6,904,818 B2 | 6/2005 | Harthorn et al. | |
| 6,975,108 B2 | 12/2005 | Bilik et al. | |
| 7,082,822 B2 | 8/2006 | Harthorn et al. | |
| 7,104,125 B2 | 9/2006 | Harthorn et al. | |
| 7,155,369 B2 | 12/2006 | Papadimitriou et al. | |
| 7,159,654 B2 | 1/2007 | Ellison et al. | |
| 7,231,320 B2 | 6/2007 | Papadimitriou et al. | |
| 7,241,349 B2 * | 7/2007 | Takahashi | 148/509 |
| 2003/0140710 A1 * | 7/2003 | Nakayama et al. | 73/841 |
| 2003/0229476 A1 | 12/2003 | Naganarayana et al. | |
| 2004/0225474 A1 | 11/2004 | Goldfine et al. | |
| 2005/0127908 A1 | 6/2005 | Schlicker et al. | |

* cited by examiner

---

The minimum GAIN of the PGA is:    G = 1 + [R3 / (R2 + R1)]

The maximum GAIN of the PGA is:    G = 1 + [R3 /R2]

---

EXAMPLE 1:

R1 = 100K         R2 = 5K         R3 = 100K

Maximum GAIN = 21         Minimum GAIN = 1.95

---

EXAMPLE 2:

R1 = 100K         R2 = 1K         R3 = 100K

Maximum GAIN = 101         Minimum GAIN = 1.99

---

1st Order Filter
Transfer Function:  $H(s) = 1 / (s + \omega_c)$

*Design Equation:*  $R1 = 1 / [2\ K\ \pi\ C1\ F_c] = 1 / [K\ C1\ \omega_c]$

---

2nd Order Filter
Transfer Function:  $H(s) = 1 / [s^2 + s\ a\ \omega_c) + \omega_c^2]$ Design Equations:  $G = 3 - a$ $R2 = 1 / [2\ K\ \pi\ C2\ F_c]$ $R4 = 2\ G\ R2 \qquad R3 = R4 / [G - 1]$ Where:
    Fc = Cutoff Frequency      K, a = Filter Type Constants

---

1st Order Filter

Transfer Function:   $H(s) = s / (s + \omega_c)$

*Design Equation:*   $R1 = 1 / [2 \, K \, \pi \, C1 \, F_c] = 1 / [K \, C1 \, \omega_c]$

---

2nd Order Filter

Transfer Function:  $H(s) = s^2 / [s^2 + s \, a \, \omega_c) + \omega_c^2]$

Design Equations:   $G = 3 - a$ $R2 = 1 / [2 \, K \, \pi \, C2 \, F_c]$ $R4 = 2 \, G \, R2$        $R3 = R4 / [G - 1]$ Where:
   Fc = Cutoff Frequency        K, a = Filter Type Constants

Transforming ANALOG FILTERS to equivalent INFINITE IMPULSE RESPONSE (IIR) DIGITAL FILTERS

A typical analog filter transfer function is of the form:

$$H(s) = \frac{\sum_{i=0}^{m} a_i s^i}{\sum_{i=0}^{n} b_i s^i} = \frac{N(s)}{D(s)} \qquad \text{(Eq. 11.1)}$$

where m is less or equal to n

Each of the Numerator N(s) and Denominator D(s) polynomials is transformed separately by substituting the variable (s) as shown in equation 11.2.

Higher orders of digital filters are obtained by cascading $1^{st}$ and $2^{nd}$ order digital filter.

FIG. 11A

BILINEAR TRANSFORMATION

Bilinear Transformation is a frequency domain method particularly suited for the design of recursive digital filters, commonly known as IIR Digital filters, by converting an analog filter transfer function H(s) into an equivalent digital transfer function H(z). The Bilinear Transformation is performed by substituting variables:

$$s = 2 * Fs * \frac{(z-1)}{(z+1)} \qquad \text{(Eq. 11.2)}$$

where Fs is the Sampling Frequency.

FIG. 11B

The frequency response of the IIR Digital filter is obtained by substituting:

$$z = e^{j\omega/Fs} \qquad \text{(Eq. 11.3)}$$

FIG. 11C

WAVELETS

For discrete time samples, the wavelet transform can be accomplished by applying filter banks. A typical decomposition filter bank is shown below.

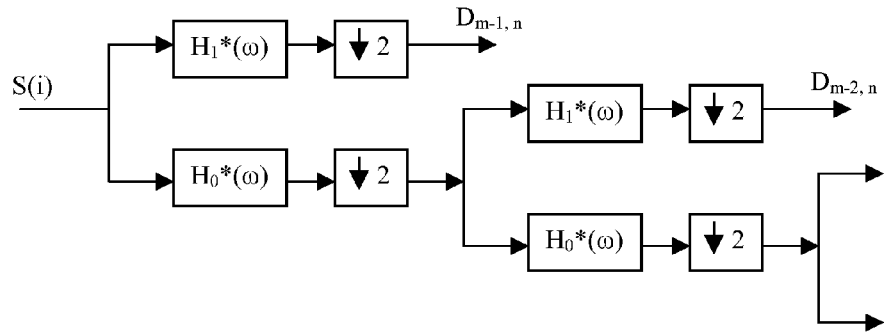

Where S(i) is the original signal $D_{m,n}$ are wavelet series coefficients and

[↓2] *denotes downsampling by 2.*

For example, the HAAR wavelet $$H_0(\omega) = 0.5(1 + e^{-j\omega}) \qquad \text{(Eq. 12.1)}$$

describes a low-pass where $H_0(0) = 1$ and $H_0(\pi) = 0$.

The quadrature mirror filter of $H_0(\omega)$ is $H_1(\omega)$ $$H_1(\omega) = 0.5(1 - e^{-j\omega}) \qquad \text{(Eq. 12.2)}$$

describes a high-pass filter.

FIG. 12C

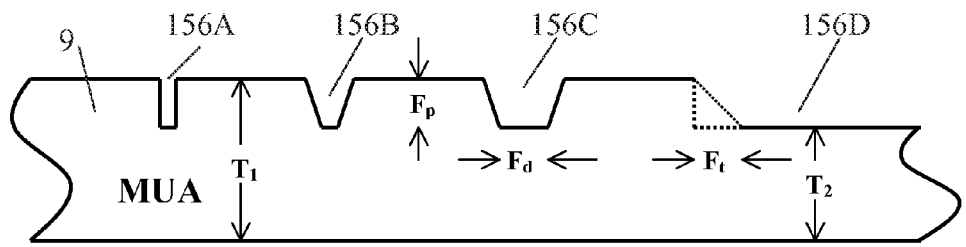
FIG. 16A
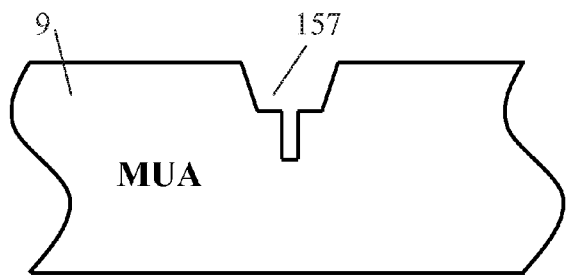
FIG. 16B
| Typical 1D-NDI Recommended Reference & Disposition Standards ||||||
| Reference Imperfection | Length || Width || Depth ||
| | inches | tolerance | inches | tolerance | % penetration | tolerance |
| 1/16" Hole | 0.063" | ±0.016" | 0.063" | ±0.016" | 100% | – |
| 5% Notch | 1.000" | -0.500" | 0.040" | – | 5% | ±0.004" |
| 10% Notch | 0.500" | – | 0.020" | or less | 10% | ±1.5% |
| Wall Loss | – | – | – | – | 12.5% | – |
FIG. 16C
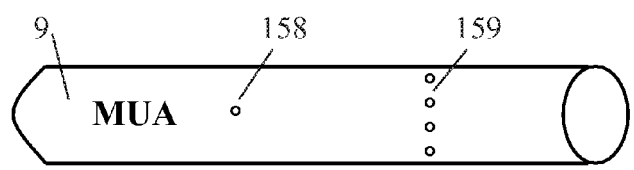
FIG. 16D

AUTONOMOUS FITNESS FOR SERVICE ASSESSMENT

RELATED APPLICATIONS

This application is a continuation in part of U.S. patent application Ser. No. 10/867,004 having a filing date of Jun. 14, 2004 now U.S. Pat. No. 7,240,010 and a continuation in part of U.S. patent application Ser. No. 10/995,692 having a filing date of Nov. 22, 2004 (U.S. Pat. No. 7,155,369) and a continuation in part of U.S. patent application Ser. No. 11/079,745 having a filing date of Mar. 14, 2005 (U.S. Pat. No. 7,231,320) and a continuation in part of U.S. patent application Ser. No. 11/743,550 having a filing date of May 2, 2007 now U.S. Pat. No. 7,403,871 and a continuation in part of U.S. patent application Ser. No. 11/769,216 having a filing date of Jun. 27, 2007 now U.S. Pat. No. 8,086,425 and a continuation in part of U.S. patent application Ser. No. 11/772,357 having a filing date of Jul. 2, 2007 now U.S. Pat. No. 8,050,874, and a divisional of U.S. patent application Ser. No. 11/769,216 having a filing date of Jun. 27, 2007 now U.S. Pat. No. 8,086,425. Each and every patent and application listed above is hereby incorporated by reference.

TECHNICAL FIELD

This invention relates, generally, to non-destructive fitness for service assessment method and equipment, and more specifically, to provide automatic and/or continuous non-destructive acquisition of material features, including evaluators and predictors of detected features, and autonomous evaluation capability of the material fitness for continuing reliable use.

BACKGROUND OF THE INVENTION

As is known in the art, materials are selected for use based on criteria including minimum strength requirements, useable life, and anticipated normal wear. Safety factors are typically factored into the design considerations to supplement material selection in order to aid in reducing the risk of failures including catastrophic failure. Failures occur when the required application strengths exceed the actual material strength either due to the misapplication of the material or due to material deterioration. During its useful life, material deteriorates and/or is weakened by external events such as mechanical and/or chemical actions arising from the type of application, repeated usage, hurricanes, earthquakes, storage, transportation, and the like; thus, raising safety, operational, functionality, and serviceability issues. The list of typical material includes, but is not limited to, aircraft, bridges, cranes, drilling rigs, frames, chemical plant components, engine components, oil country tubular goods (herein after referred to as "OCTG"), pipelines, power plant components, rails, refineries, rolling stoke, sea going vessels, service rigs, structures, vessels, workover rigs, other components of the above, combinations of the above, and similar items.

Material owners perform a fitness for service (herein after referred to as "FFS") assessment occasionally, often following a component failure. This FFS assessment is mostly based on as-designed data occasionally supplemented by Non-Destructive Inspection (herein after referred to as "NDI") data. Often, the absence of an NDI indication comprises the entire FFS assessment. NDI is typically carried out in order to verify that the material deterioration, from some of the known deterioration causes, has not reduced the material strength below the minimum application requirements.

Since its inception in the early 1900s, the NDI industry has utilized a variety of techniques and devices, alone or in combination with each other, with the majority based on the well known and well documented techniques of magnetic flux leakage (herein after referred to as "MFL"), eddy-current (herein after referred to as "EC"), magnetic particle, ultrasonic (herein after referred to as "UT") radiation, such as x-ray and gamma ray, dye penetrant, and dimensional as well as visual and audible techniques. MFL and EC are also known as ElectroMagnetic Inspection (herein after referred to as "EMI"). Typical NDI devices deploy a single sensor per material area and are therefore classified as one-dimensional (herein after referred to as "1D", "1D-NDI" and "1D-EMI").

However, the limited data 1D-NDI provides for the Material-Under-Inspection (herein after referred to as "MUI") does not adequately address the demanding material application FFS needs. After all, a century ago there was no drilling a 20,000-foot well in 10,000 feet of water in search for hydrocarbons or trains traveling at speeds in excess of 100 miles per hour or supersonic aircraft. For example, when 1D-NDI does not detect any corrosion pitting that exceeds its minimum detection capabilities, it is false to conclude that the material is fit for the application. It is desirable therefore to provide Autonomous FFS (herein after referred to as "AutoFFS") equipment and methods to the industry. AutoFFS must detect and recognize the "as-built" and/or "as-is" MUI features impacting its FFS including, but not limited to, imperfections.

The Distinction Between FFS Assessment and NDI

As carried out since its inception, NDI is examining the MUI for signals (flags) that exceed a preset threshold level while common MUI features, such as welds and couplings, typically saturate the NDI processing and they are ignored. Therefore, the end result of an NDI can be summarized as "within the limitations of the inspection technique(s), there were no material regions that gave rise to signals above the threshold level". As will be discussed further, the combination of sensor signal filtering and threshold prior to any signal evaluations creates detection dead-zones, a standard NDI practice never the less. Such filter/threshold combination can be found throughout the patent record, such as in the 1931 U.S. Pat. No. 1,823,810 and the 2003 U.S. Pat. No. 6,594,591. Therefore, the absence of an NDI indication does not necessarily imply that the material is fit for service.

Another example of an NDI technique with different type detection dead-zones is Time of Flight Diffraction (herein after referred to as "TOFD") of U.S. Pat. Nos. 6,904,818, 7,082,822, 7,104,125 used for the inspection of marine drilling risers. The near-surface TOFD dead zone is due to lateral waves and the far-surface TOFD dead zone is due to echoes. It should be noted that the major and minor axis surfaces of marine drilling risers experience the maximum vortex-induced-vibration (herein after referred to as "VIV") loads and thus, cracking is expected to initiate at stress concentrators within the TOFD dead-zones, like the bottom of surface pits or the heat affected zone of welds. From actual fatigue and crack growth field runs, Stylwan has concluded that weld cracks tend to grow preferentially parallel to the surface (increase length) than into the wall (increase depth) and therefore would remain undetected by TOFD while undergoing their most rapid growth. The TOFD dead-zones are significant on used material, typically exceeding the maximum allowed imperfection depth. Therefore, the absence of a TOFD indication can be summarized as "there were no material regions with cracks deeper than the TOFD detection dead-zones" which by no means constitute a sound NDI on used material much less an FFS assessment.

On the other hand, FFS must examine and evaluate, as close as possible, 100% of the Material-Under-FFS-Assessment (herein after referred to as "MUA") for 100% of features spanning from fatigue (2-D) all the way to wall thickness changes (A-WDS) and declare the MUA fit for continuing service only after all the features impact upon the MUA have been evaluated. It is well known that the presence of any imperfection alters the FFS of the MUA and impacts its remaining useful life. Thus, it should be appreciated that the deployment of the AutoFFS would increase the overall safety and reliability as it would lead to MUA repair and/or replacement prior to a catastrophic failure as well as it will reduce and/or eliminate its premature replacement due to concerns when the conventional inspection periods are spaced far apart and/or when the conventional inspection provides an insignificant inspection coverage. In addition, it should be understood that material free of any imperfections may still not be fit for service in the particular application and/or deployment.

There is a plethora of 1D-NDI systems in the patent record using terms such as, "Detect", "Identify", "Recognize" but only in the context that the sensor signal exceeds the preset threshold level and an indication is shown in the 1D-NDI readout device. The 1D-NDI readout device indication prompts the inspector to assign the material to the verification crew for further manual investigation. However, 1D-NDI cannot "connect or associate or know by some detail" the feature or even if the sensor signal is indeed associated with a feature; a task assigned entirely to the manual verification crew. As opposed to 1D-NDI, the present invention also uses terms such as, "Identify" and "Recognize" in the context of "connect or associate or know by some detail". AutoFFS "knows by some detail" the imperfection and "connects and associates" the imperfection with known imperfection definitions. AutoFFS preferably uses fitness for service formulas and knowledge and is preferably able to export a file for use by an FEA engine because AutoFFS "knows by some detail" the material features. It should be understood that different FEA engines use different structure geometry import/export specifications.

SUMMARY OF THE INVENTION

In one possible embodiment, an evaluation system may be provided to ascertain and/or to mitigate hazards arising from the failure of a material resulting from misapplication and/or deterioration of the material. The system may comprise elements such as, for instance, a computer and a material features acquisition system. The materials feature acquisition system may be used to scan the material and identify the nature and/or characteristics of material features. In one possible embodiment, the invention may further comprise a database which may comprise material historical data and/or constraints. The first database constraints may be selected at least in part from knowledge and/or rules. The knowledge and/or rules may involve stress or loading related factors. A non-limiting list of knowledge or rules may involve use of the material in applications involving one or more of bending, buckling, compression, cyclic loading, deflection, deformation, dynamic linking, dynamic loading, eccentricity, eccentric loading, elastic deformation, energy absorption, feature growth, feature morphology migration, feature propagation, impulse, loading, misalignment, moments, offset, oscillation, plastic deformation, propagation, shear, static loading, strain, stress, tension, thermal loading, torsion, twisting, vibration, and/or a combination thereof.

In another embodiment, a first computer program may evaluate the impact of the material features upon the material by operating on the material features. The operation may be guided by the database constraints and/or any material historical data. In one possible embodiment, the first computer program evaluates the fitness for service of the material under the constraints.

In another possible embodiment, a material evaluation system may comprise a computer, a material features acquisition system, a first database comprising of constraints and/or material historical data; and/or a data conversion program, whereby the material features may be rendered in a data format for use by a finite element analysis engine.

In another possible embodiment, the invention may comprise a sensor with an output comprising of signals indicative of features from the material being scanned, in a time-varying electrical form. A sensor interface may be provided for the computer, wherein the computer converts the signals to a digital format. Additional elements may comprise at least one database comprising of material features recognition constraints and/or historical data. A computer program may be executed on the computer for identifying the material features detected by said sensor.

These and other embodiments, objectives, features, and advantages of the present invention will become apparent from the drawings, the descriptions given herein, and the appended claims. However, it will be understood that above-listed embodiments and/or objectives and/or advantages of the invention are intended only as an aid in quickly understanding certain possible aspects of the invention, are not intended to limit the invention in any way, and therefore do not form a comprehensive or restrictive list of embodiments, objectives, features, and/or advantages.

BRIEF DESCRIPTION OF THE DRAWINGS

FIG. 11A illustrates the Bilinear Transformation, a mathematical technique to translate an analog transfer function to the digital domain, according to the present invention;

FIG. 11B illustrates the mathematical formula for the Bilinear Transformation illustrated in FIG. 11A according to the present invention;

FIG. 11C illustrates a mathematical formula for the frequency response of IIR Digital filter for the Bilinear Transformation illustrated in FIG. 11A according to the present invention;

FIG. 12A illustrates the block-diagram to implement the discrete wavelet transform decomposition through digital filter banks according to the present invention;

FIG. 12B illustrates a mathematical formula for a low-pass filter of a HAAR wavelet of FIG. 12A according to the present invention;

FIG. 12C illustrates a mathematical formula for a high-pass filter of a HAAR wavelet of FIG. 12A according to the present invention;

FIG. 16A illustrates a typical material sample with man-made features;

FIG. 16B illustrates a typical material sample with a critically flawed area;

FIG. 16C illustrates typical reference defects found in 1D-NDI standards;

FIG. 16D a critically flawed area;

DETAILED DESCRIPTION OF EMBODIMENTS OF THE INVENTION

Figure 1:
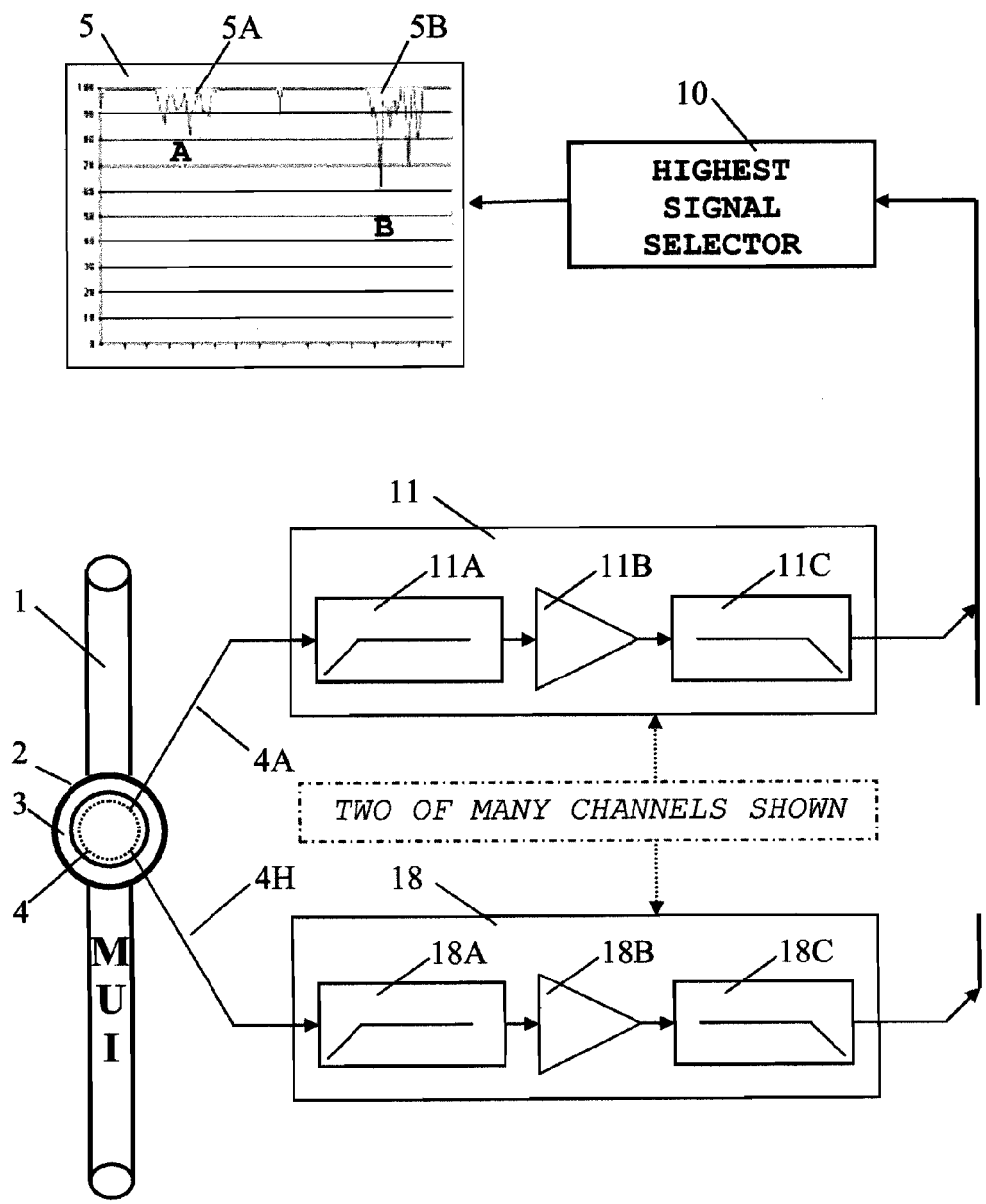
FIG. 1 illustrates a block diagram of a 1D-EMI non-destructive inspection system.

The following Trademarks are referred to herein below in alphabetical order:

Compact Flaw Spectrum, CoilBOT, CyberCHECK, CyberInspector, CyberSCAN, CyberSCOPE, Defect Numerical Analysis, Flaw Defining Dimension, FDDim, Flaw Spectrum, InspectionBOT, LineBOT, Material Status Descriptive Value, MSDV, RailBOT, Rig Data Integration System, RDIS-10, RiserBOT, STYLWAN and WellBOT are trademarks of STYLWAN Incorporated.

OCI-5000 series and OCI are trademarks of OLYMPIC CONTROL, Incorporated.

To understand the terms associated with the present invention, the following descriptions are set out herein below. It should be appreciated that mere changes in terminology cannot render such terms as being outside the scope of the present invention.

Autonomous: able to perform a function without external control or intervention.

Classification: assigning a feature to a particular class.

Compact Flaw Spectrum: a condensed presentation of Flaw Spectrum or Frequency Flaw Spectrum data. The STYLWAN Compact Flaw Spectrum and trace color assignments is set out herein below and spans from wall thickness (3-DC) to microcracking (2-DC): C-3D (blue), C-3d (green), C-2d (red) and C-2D (magenta) and Geometry variations 3-G (yellow).

Constraints: controls in doing something. Constraints include, but are not limited to knowledge, rules, boundaries and data.

Decomposed in Frequency: Separating desirable characteristics from a frequency response gathered during an evaluation process.

Defect: an imperfection that exceeds a specified threshold and may warrant rejection of the material.

Degradation Mechanism: the phenomenon that is harmful to the material. Degradation is typically cumulative and irreversible such as fatigue built-up.

Essential: important, absolutely necessary.

Expert: someone who is skilful and well informed in a particular field.

Feature: a property, attribute or characteristic that sets something apart.

Finite Element Analysis: a method to solve the partial or ordinary differential equations that guide physical systems, (herein after referred to as "FEA").

FEA Engine: is an FEA computer program, a number of which are commercially available such as Algor and Nastran. In practice, FEA engines are used to analyze structures under different loads and/or conditions, such as a marine drilling riser under tension and enduring vortex induced vibration. An FEA engine may analyze a structure with a feature under static and/or dynamic loading, but not a feature on its own.

Fitness For Service: typically an engineering assessment to establish the integrity of in service material, which may or may not contain an imperfection, to ensure the continuous economic use of the material, to optimize maintenance intervals and to provide meaningful-remaining useful life predictions. In the prior art, FFS assessment was typically performed by an expert or a group of experts. Typically, an FFS assessment is based primarily on as-designed data while the AutoFFS assessment is based primarily on as-built or as-is data. When design data is available, AutoFFS also monitors compliance with the design data. When less than optimal data is available, AutoFFS may perform a Fitness For Service Screening.

Flaw Defining Dimension: (Herein after referred to as "FDDim") typically the flaw dimension and/or projection perpendicular (transverse) to the maximum stress. The extraction matrix calculates FDDim. The extraction matrix was published in 1994 and it is beyond the scope of this patent.

Flaw Spectrum: a presentation of data derived from an extraction matrix. The STYLWAN Flaw Spectrum and trace color assignments is set out herein below and spans from wall thickness (A-WDS) to microcracking (2-D): A-WDS (maroon), R-WDS (black), 3-D (blue), 3-d (cyan), C (green), 2-d (red) and 2-D (magenta) and Geometry variations 3-G (yellow). When necessary, categories are further subdivided to $\alpha$, $\beta$ and $\gamma$, such as 2-da. It should be understood that the one to one correspondence of simple imperfections to the STYLWAN Flaw Spectrum occasionally applies to machined (man-made) imperfections and not to the complex form imperfections typically found in nature. Therefore, the STYLWAN Flaw Spectrum elements must be viewed as an entity identification signature, just like DNA, but not as a detailed chemical analysis. It should be appreciated that mere changes in terminology and/or regrouping and/or recategorizing cannot render such terms as being outside the scope of the present invention.

Frequency Based Flaw Spectrum: a presentation of data derived from one-dimensional or two-dimensional sensor in combination with filter banks to decompose, interpret and categorize the sensor received information in a fashion substantially similar to the flaw spectrum. It should be understood that any further processing, such as the AutoFFS processing, utilizes, the Flaw Spectrum regardless of its origin and derivation method.

Imperfection or Flaw: one of the material features—a discontinuity, irregularity, anomaly, inhomogenity, or a rupture in the material under inspection.

Knowledge: a collection of facts and rules capturing the knowledge of one or more specialist.

Normalization: Amplitude, and/or phase, and/or bandwidth, and/or time shifting adjustments of the inspection sensor output to compensate for the system implementation idiosyncrasies that affect the features sensor output such as changes/differences due to scanning speed and/or implementation geometry and/or excitation and/or for response characteristics of the inspection sensor.

Productivity: The total amount of material undergone assessment or evaluation. The productivity rate is defined as the ratio of amount of material undergone assessment or evaluation over the amount of time to perform such assessment or evaluation.

Remaining Useful Life: a measure that combines the material condition and the failure risk the material owner is willing to accept. The time period or the number of cycles material (a structure) is expected to be available for reliable use.

Remaining Useful Life Estimation (herein after referred to as "RULE"): establishes the next monitoring interval (condition based maintenance) or the need for remediation but it is not intended to establish the exact time of a failure. When RULE can be established with reasonable certainty, the next monitoring interval may also be established with reasonable certainty. When RULE cannot be established with reasonable certainty, then RULE may establish the remediation method and upon completion of the remediation, the next monitoring interval may be established. When end of useful life is established with reasonable certainty, alteration and/or repair and/or replacement may be delayed under continuous monitoring.

Response Characteristics Desirable characteristics separated from a frequency response to be evaluated preferably by a computer to determine imperfections.

Rules: how something should be done to implement the facts.

Scanning Speed The speed of the material passing the sensor (or the speed of the sensor along the material).

1D-EMI Inspection Equipment Description

Figure 5:
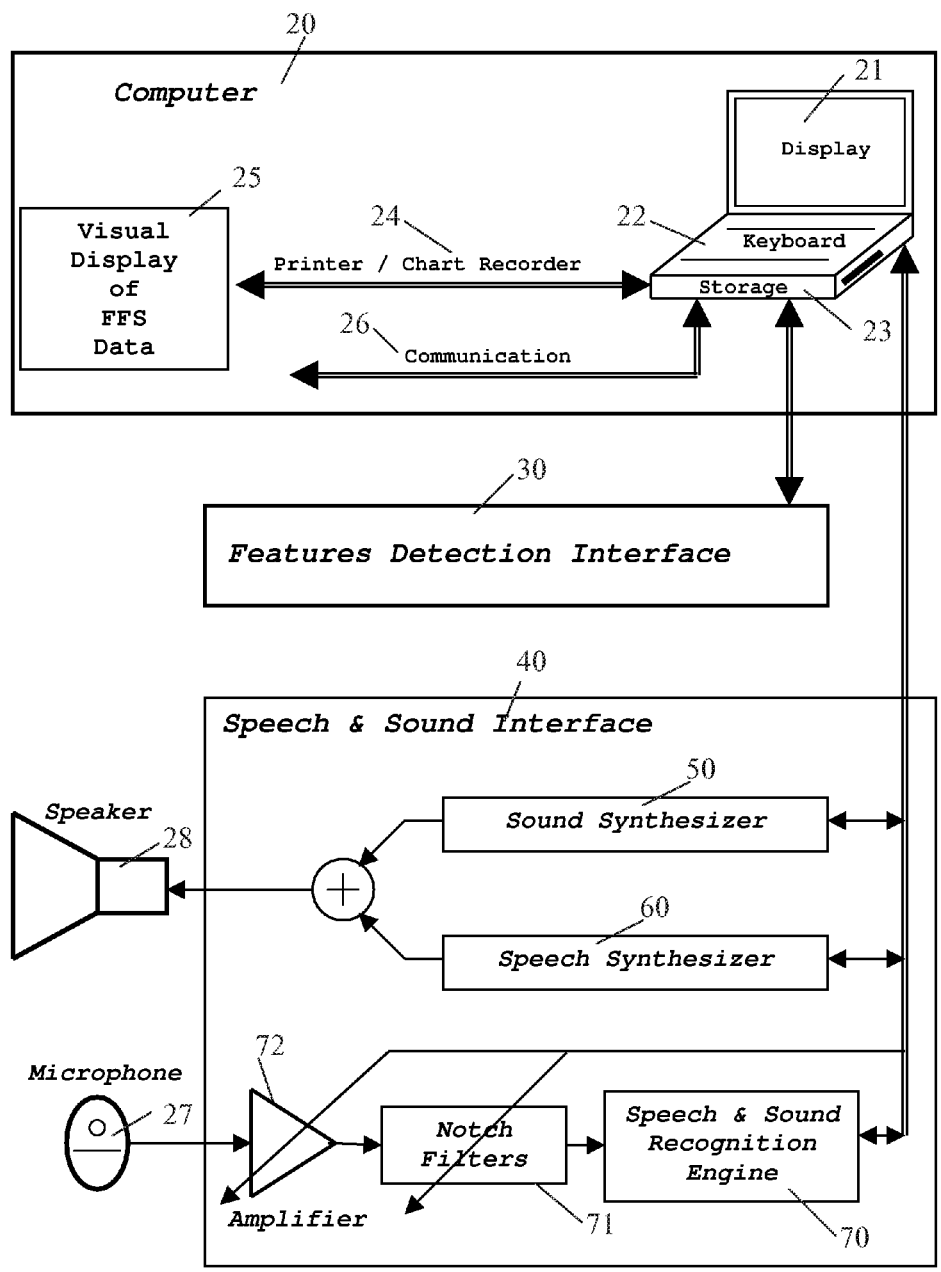
FIG. 5 illustrates a block diagram of the AutoFFS system and the speech and sound interface according to the present invention.
Figure 6:
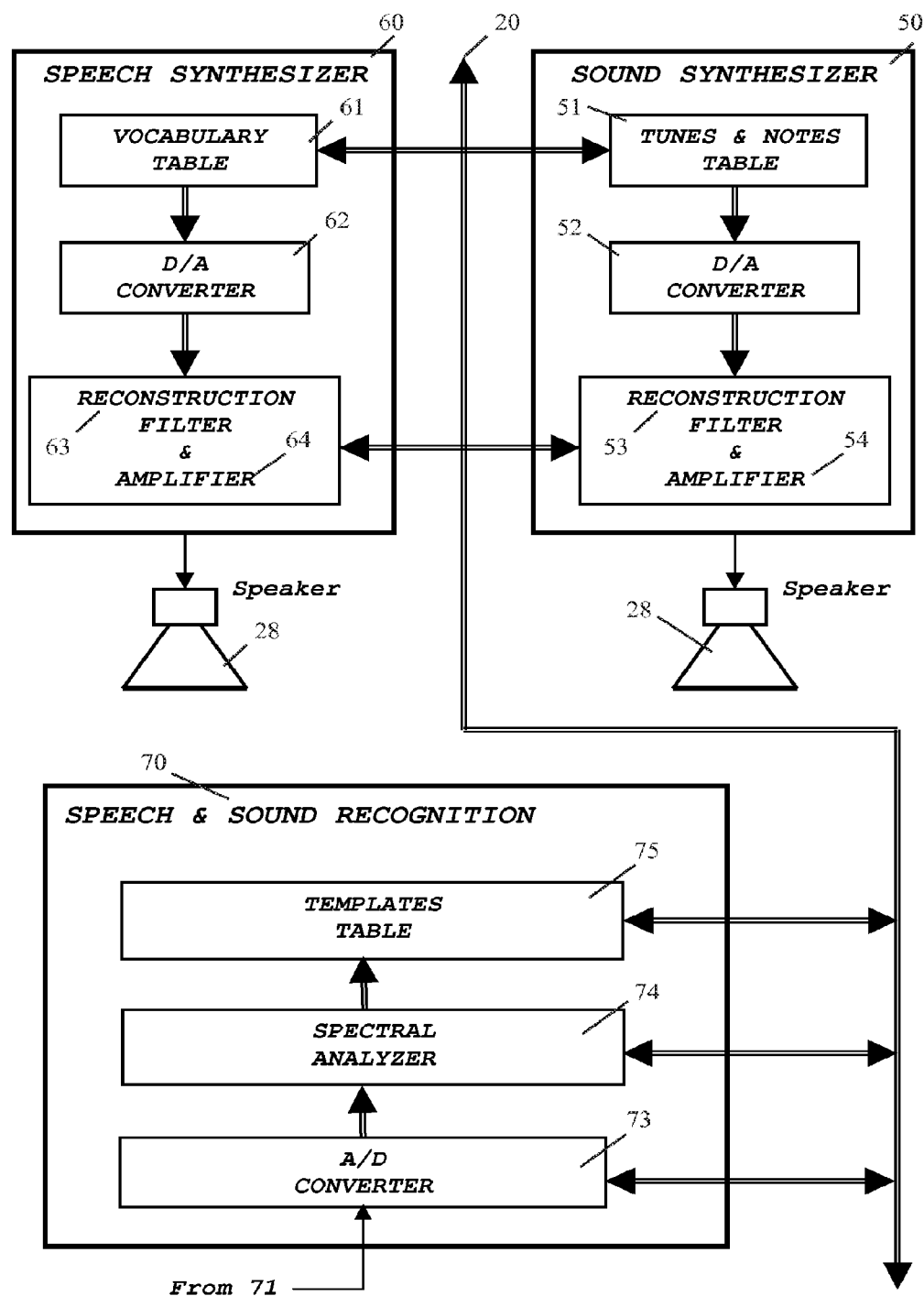
FIG. 6 illustrates a block diagram of a speech synthesizer, a sSound synthesizer and a Speech recognition engine.
Figure 7:
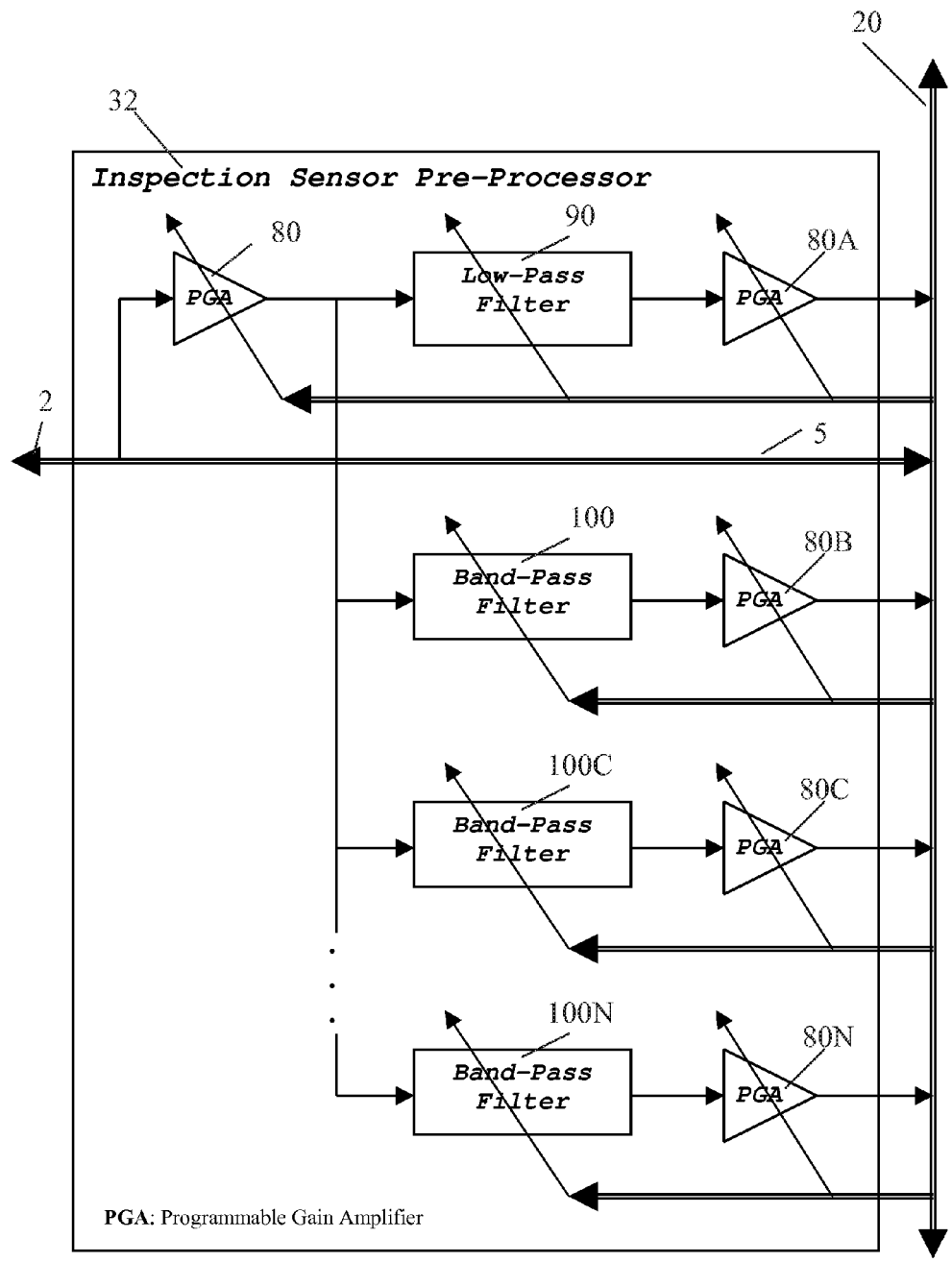
FIG. 7 illustrates a block-diagram of the inspection sensor pre-processor and the filter arrangement according to the present invention.

FIG. 1 illustrates a block diagram of an eight channel 1D-EMI inspection system similar to the one in U.S. Pat. No. 2,685,672 utilizing the MFL principle. In particular, the sensors and their arrangement as described in 672 FIGS. 5 and 6 are still in use with hundreds of units employed worldwide in portable or stationary configurations. The same sensor configuration is also illustrated in FIG. 7 of U.S. Pat. No. 2,881, 386 and similar sensors configuration is also used in the pipeline pig of U.S. Pat. No. 3,225,293.

The magnetizing coil 3 of the inspection head 2 induces excitation into MUI 1. It should be understood that the magnetic field can be applied in any direction. U.S. Pat. No. 2,685,672 shows the induction of a longitudinal magnetic field while U.S. Pat. No. 3,202,914 shows the induction of a transverse magnetic field. It should further be understood that one or more permanent magnets may be use instead of a magnetizing coil or a combination thereof. The inspection sensors 4 signals 4A through 4H are processed by the high-pass filters 11A through 18A to eliminate low frequencies and any dc components. The signals 4A through 4H are then amplified by amplifiers 11B through 18B and are then filtered by the low-pass filters 11C through 18C to eliminate high frequencies. The highest signal selector 10 compares the highest of the band-limited signals 4A through 4H to a preset threshold level and eliminates all signals below the threshold level. Thus, the inspection trace 5 that is presented to the inspector typically shows the frequency band-limited highest signal that exceeds a preset threshold level. This type of signal acquisition and processing creates detection dead-zones and it is not suitable for FFS assessment or screening.

The MFL principle of operation is eloquently described in U.S. Pat. No. 2,194,229: "It is old in the art to test magnetic material for flaws by passing therethrough a magnetic flux, providing means responsive to variations in the flux, and thereby locating regions of abnormal magnetic reluctance"; and herein lies the problem that has plagued the 1D-NDI all along. 1D-EMI units flag " . . . regions of abnormal magnetic reluctance" in ferromagnetic materials and UT units flag regions of echoes. They do not identify the material features; they do not detect the failure-potential of any feature, including but not limited to imperfection, and most importantly, they do not assess the material fitness for service under the application constraints. Instead, they rely upon an inspector to monitor and interpret the MFL or UT traces and instruct a manual verification crew to locate the flagged " . . . regions of abnormal magnetic reluctance" or echoes on the MUI for further manual investigation, but only for MUI regions that give rise to signals that exceed a preset magnitude threshold, a 1D-NDI shortcoming that can still be found, for example, in U.S. Pat. No. 6,594,591 FIG. 9 and will be discussed in detail further below. Thus, OCTG owners typically specify that the verification crew investigate at least ±six inches on either side of an indication. It is not uncommon for the verification crew to miss entirely the flagged MUI region or even the flagged MUI from a simple miscount. This manual verification problem is exemplified on pipelines that are miles long or railroads, a two vehicle inspection/verification solution described in U.S. Pat. No. 5,970,438.

Once an imperfection is located by the verification crew and sufficient measurements are recorded, the information is forwarded to the owner of the MUI to decide its disposition. In order to decide the disposition of the MUI, the owner preferably performs an FFS assessment with the limited data the verification crew was able to gather. Often, a single pass/fail approach is implemented.

It is therefore desirable to provide means to retrofit AutoFFS to the hundreds of 1D-EMI units deployed worldwide. It is imperative therefore, that AutoFFS detects and recognizes the "as-is" MUA features impacting its FFS including, but not limited to, imperfections. The imperfection recognition was discussed in the AutoNDI prior application Ser. No. 10/995,692 (U.S. Pat. No. 7,155,369) using the extraction matrix and application Ser. No. 11/079,745 (U.S. Pat. No. 7,231,320) using spectral analysis to derive a frequency based flaw spectrum for further use by the AutoNDI.

A Brief 1D-EMI History

The one to one correspondence of FIG. 1 1D-EMI elements to the elements illustrated in FIG. 1 of U.S. Pat. No. 1,823,810 is as follows: A magnetic field (excitation) is induced into MUI 1 (810 FIG. 1 magnetizable material 6) by a coil 3 (810 FIG. 1 exciting coil 14). The sensor 4 (810 FIG. 1 search coil 19) signal is processed by the high-pass filter 11A (810 FIG. 1 capacitor and resistor connected to the grid of the vacuum tube) and it is then amplified by amplifier 11B (810 FIG. 1 dual triode vacuum tube) and presented to the inspector (810 FIG. 1 indicator 21) instead of an inspection trace 5. The limited frequency response of (810 FIG. 1 indicator 21) acts as a lowpass filter 11C. Since U.S. Pat. No. 1,823,810 depicts a single channel NDI system, there is no need for a highest signal selector 10. However, the sensor 4 (810 FIG. 1 search coil 19) signal is compared to an operator adjustable threshold level (810 FIG. 1 the resistor connected to the grid of the first vacuum tube is connected to a negative (threshold) voltage). Only sensor signals that exceed this threshold (negative voltage) would propagate and be shown to the inspector (810 FIG. 1 indicator 21).

The prolific 1D-EMI unit of U.S. Pat. No. 2,685,672 essentially consists of eight U.S. Pat. No. 1,823,810 channels with the addition of a highest signal selector. It should be understood that 1D-EMI units consisting of two to forty eight channels have also been constructed and the number of channels any 1D-EMI deploys should not be interpreted as a limitation to this invention. In the 1960s the vacuum tubes were replaced by transistors, as shown in U.S. Pat. No. 3,202,914 FIG. 6, and in the 1970s by integrated circuit amplifiers. Meters and chart recorders were used for the operator readout until the mid 1980s when they were replaced by computers with their colorful displays and printouts. However, no matter how sophisticated the operator readout is, it will never show information lost during the acquisition and processing of the sensor signals.

The brief 1D-EMI history shows that although the electronic circuits have followed the advances in technology, the inspection philosophy and methods have not. The 1D-EMI limitations and pitfalls of a century ago still plague the modern 1D-EMI, regardless of the inspection technique used. For example, U.S. Pat. No. 6,594,591 applies the combination of sensor signal filtering and threshold prior to any signal evaluation to both EMI and UT.

1D-EMI Loss of Sensor Signal Frequency Spectrum Information

As discussed earlier, the 1D-EMI high-pass filters 11A through 18A eliminate low frequencies and dc components for system stability and the low-pass filters 11C through 18C to eliminate high frequencies to remove the "noise". Useful frequency components of the sensor signal are therefore discarded before being evaluated and any useful information they may contain is prematurely and irreversibly lost rendering this type of signal acquisition and processing unsuitable for AutoFFS. Referring to FIG. 6 of U.S. Pat. No. 3,202,914, capacitor 51 and its associated components form a high-pass filter that prematurely and irreversibly discards low-frequency components of the sensor signal while capacitor 48 and its associated components form a low-pass filter that prematurely and irreversibly discards high-frequency components of the sensor signal. Other such examples can be found in U.S. Pat. No. 2,582,437 (see FIG. 1 capacitor 13 and resistor 40); in U.S. Pat. No. 1,823,810 (see FIG. 1, amplifier 20) as well as in U.S. Pat. No. 5,671,155 (see FIG. 1, AC-couplers 6) and U.S. Pat. No. 5,943,632 (see FIG. 1, AC-couplers 6). Another such example using digital filters is shown in FIG. 8 of U.S. Pat. No. 5,371,462 showing a " . . . flow chart of an algorithm for pre-processing to remove DC and low frequency components" from the sensor signal.

Scanning Speed Effects on the Sensor Signal

U.S. Pat. No. 2,770,773 also encompasses many elements of the above to detect corrosion pitting and clearly states a frequency spectrum processing essential element: the imperfection frequency spectrum versus scanning speed interdependence. The high-pass filters of FIG. 7 (capacitors 66, 67 and resistors 69, 70) remove many unwanted. " . . . signal producing variables such as separation from the casing wall, wall roughness, misfit . . . " [Column 6, Line 15]. Following the high-pass filter is a band-pass filter " . . . to pass frequencies in the band between about 3 and 20 cycles per second, as this is the characteristic frequency range of signal due to the passage of the shoe 15 across a casing corrosion pit at a transverse speed of twenty feet per minute. This frequency band related to the speed of traverse of the instrument 10 through the casing 12 will, of course, be varied to suit any other traverse speed selected" [Column 6, Line 33]. Therefore, it is well known in the art that the same imperfection will appear differently in the sensor signal frequency spectrum depending on the scanning speed. It is also well known in the art that fixed frequency filters always pass/discard the same frequency band, thus 1D-EMI systems, such as the ones in U.S. Pat. Nos. 5,671,155 and 5,943,632, always propagate for further processing undefined frequency components of the sensor signal again, rendering this type of signal acquisition and processing unsuitable for AutoFFS.

Another early observation of the NDI industry is the scanning speed versus signal amplitude proportional interdependence for coil sensors. U.S. Pat. No. 2,881,386 (see FIGS. 10 and 11) provides a technique for amplitude compensation for the scanning speed variations.

AutoFFS can only be carried out when the MUA features, including but not limited to imperfections, are recognized and are identified. Automatic features recognition demands that the features signal amplitude and frequency spectrum be compensated for the idiosyncrasies of the scanning system and the effects of the different scanning speeds. It is one possible objective of this embodiment of the invention to determine the inspection system response characteristics, to track the scanning speed and preserve, normalize and automatically analyze the sensor signal frequency spectrum for all the spectrum components that include non-redundant information spanning from Fatigue to wall thickness.

1D-NDI Calibration Limitations

Figure 2A:
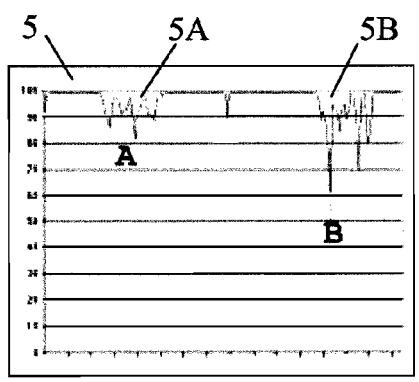
FIG. 2A illustrates a 1D-EMI inspection trace for a mid-wall imperfection.

FIG. 2A illustrates the 1D-NDI inspection trace 5 of an OCTG that failed at imperfection 5B. The OCTG had two mid-wall imperfections 5A and 5B and failed during hydrotesting. Prior to assembly into a marine drilling riser, the OCTG was inspected by a state of the art 1D-NDI. The 1D-NDI system was calibrated using a calibration joint with machined notches, a 1D inspection industry standard but faulty practice further illustrated in FIG. 16C. FIG. 2B illustrates the 1D-NDI inspection trace of a calibration notch 5C.

Figure 2C:
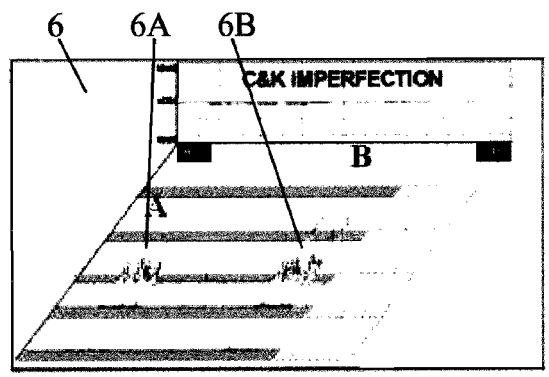
FIG. 2C illustrates the flaw spectrum of the mid-wall imperfection of FIG. 2A.
Figure 2B:
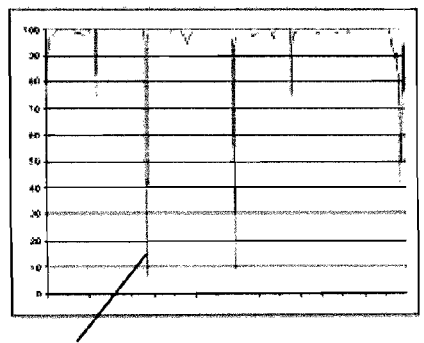
FIG. 2B illustrates a 1D-EMI inspection trace for machined (man-made) calibration notches.
Figure 2D:
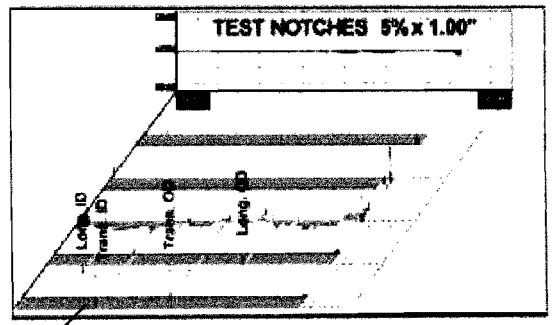
FIG. 2D illustrates the flaw spectrum of the machined (man-made) calibration notches of FIG. 2B.
Figure 3A:
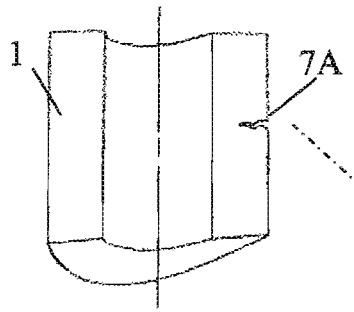
FIG. 3A illustrates a section of MUI with an imperfection.

FIG. 2C illustrates the flaw spectrum of the same OCTG mid-wall imperfections 6A and 6B, corresponding to 5A and 5B, and FIG. 2D illustrates the Stylwan flaw spectrum of the calibration notch 6C, corresponding to 5C. The reason of this failure can easily be deduced from FIGS. 2C and 2D. The Stylwan flaw spectrum of FIG. 2C clearly shows that the mid-wall imperfections 6A and 6B are utterly unrelated to the calibration notches 6C of FIG. 2D. It is also easy to see how 1D-NDI would mislead someone to believe that the mid-wall imperfections 5A and 5B of FIG. 2A are somehow related to the calibration notches 5C of FIG. 2B and setup the 1D-NDI equipment erroneously, having no way of knowing any better (Knowing that the high threshold level set by the calibration will hinder the detection of the mid-wall imperfections 5A and 5B with 1D-NDI until they burst during hydrotesting). Imperfections 5A and 5B were missed by 1D-NDI because their signal amplitude did not exceed the threshold level that was erroneously set to detect machined calibration notches. It should also be noted that when a single pass/fail measure is utilized, it would eventually lead to equipment that focus on passing the particular single measure. This is also the case with 1D-NDI. Closer scrutiny of the 1D-NDI sensor structure and signal processing would show that both are fine tuned to pass the calibration notches test while they are likely to miss imperfection 7B of FIG. 3, yet another 1D-NDI problem root cause. It is another possible objective of an embodiment of the invention to establish a scanning/inspection system calibration means and methods adept for AutoFFS 1D-NDI Remediation Limitations FIG. 3A illustrates a section of MUI with an imperfection 7A. A typical 1D-NDI remediation practice states: "An external imperfection may be removed by grinding . . . . Where grinding is performed, generous radii shall be employed to prevent abrupt changes in wall thickness . . . . The area from which the defect is removed shall be reinspected . . . to verify complete removal of the defect". This statement further illustrates the limitations of 1D-NDI.

"Grinding" actually does not "remove" an imperfection. It just shifts the imperfection 7A morphology (shape) from one with high stress concentration 8A (due to the "abrupt changes in wall thickness") to imperfection 7B with lower stress concentration 8B (due to the "generous radii"). For example, if the depth of the original external imperfection 7A was 10% of the material wall thickness, the wall loss in the OCTG region 7B would still be 10% (or greater) even after the imperfection 7A was morphed ("completely removed") into 7B by "grinding", resulting in an OCTG with altered FFS and reduced remaining-useful-life.

As discussed earlier, the 1D-EMI high-pass filters 11A through 18A eliminate low frequencies and dc components and therefore prematurely and irreversibly eliminate imperfection 7B information thus, creating "detection dead-zones" misleading great many to believe and actually verify the "complete removal of the defect", when in fact, the form-shifted "external imperfection" 7B is still clearly visible with the naked eye and the wall loss is still 10% (or more). If imperfection 7B was the result of OCTG stretching, such as a neckdown, instead of grinding, 1D-NDI would miss imperfection 7B entirely and classify the OCTG with the reduced cross sectional area erroneously. Strength of material knowledge teaches that the reduced cross sectional area of the material reduces the ability of the material to absorb energy thus altering its FFS and reduces its remaining-useful-life.

Figure 3B:
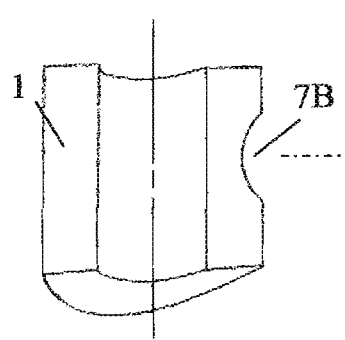
FIG. 3B illustrates a section of MUI following remediation.
Figure 3C:
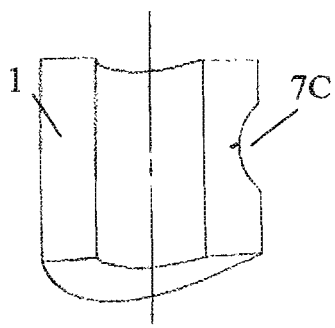
FIG. 3C illustrates a section of MUI following incomplete remediation.

FIG. 3C illustrates a dangerous condition where imperfection 7A was partially morphed leaving behind a failure seed 7C with increased stress concentration 8C. A similar example is shown in FIG. 16D element 159. 1D-NDI would miss imperfection 7C as a result of the 1D-NDI detection dead-zones arising from the combination of filters and threshold. It should be understood that this recommended 1D-NDI remediation method does not take into account the imperfection neighborhood nor does it optimize the FFS or the remaining useful life of the OCTG. It is yet another possible objective of an embodiment of the invention to establish remediation means and methods adept for AutoFFS.

1D-NDI Magnitude Threshold Versus Imperfection Pattern Recognition

As FIG. 2C illustrates, the Stylwan flaw spectrum detection of imperfections 6A and 6B is based on pattern recognition, not signal amplitude alone. Therefore, failure seeds, like imperfection 6A, can be detected early on regardless of their signal amplitude. By now, it should be easy to recognize the calibration notches 6C. However, those notches were machined on new defect-free material and they meet strict geometry standards, as it is further shown in FIG. 16C. Therefore, their flaw spectrum signature is extremely simple and easily recognizable. On the other hand, imperfections in nature are mostly found on used material, they are rarely alone, they are multifaceted and give rise to complex flaw spectrums that are not always easily recognizable. Furthermore, a key weaknesses of any manual process, such as the manual verification, is the uncontrollable "human factors". If imperfection 6A was found instead on heavily used material along with other imperfections, would a trained inspector always distinguish it in the resulting flaw spectrum clutter? It is the aim of this invention to answer this question with confidence by providing a computer, a sensor interface and a program to scan the sensor signals for patterns to recognize material features, including but not limited to imperfections. Again, features recognition demands that the frequency spectrum of the sensor signals that include non-redundant information spanning from fatigue to wall thickness is preserved and normalized.

Root Cause Identification Versus Simplistic Explanation

It should be apparent from the above that the 1D-NDI detection dead-zones, limitations and pitfalls of a century ago do not adequately address the material needs of the modern applications and they fall short in active failure prevention. Again, a century ago there was no drilling a 20,000 foot well in 10,000 feet of water in search for hydrocarbons or trains traveling at speeds in excess of 100 miles per hour or supersonic aircraft. These detection dead-zones, limitations and shortcomings of the 1D-NDI lead to a futile long term cycle as detailed below.

Often, when a failure occurs, the focus is on repairing/replacing the damaged material as rapidly as possible in order to reduce downtime and at the lowest possible cost. Occasionally, the obligatory "why?" is asked and a simplistic explanation like "fatigue cracks are a fact of life" is accepted as an adequate answer; a human decision that may lead to a catastrophic failure much later. Occasionally, an inspector or even a 1D-NDI service provider may be replaced with another one using the exact same methods and equipment. One should bear in mind the heavy dependence of 1D-NDI upon the inspector and the industry desire to preserve the 1D-NDI equipment "reputation". At some point, someone examines the number of failures over the years and discovers that there is a compatible number of failures with 1D-NDI as it is without 1D-NDI. The simplistic explanation then is that NDI is a pointless expense and it is therefore reduced or bypassed entirely; yet another human decision that may lead to a catastrophic failure much later. For example, the manufacturer and the owner of the marine drilling riser depicted in FIGS. 2A through 2D may reach such a conclusion. The compound effect of those decisions, often spanning many years, eventually leads to a spectacular catastrophic failure somewhere. The simplistic explanation for this spectacular failure is easily identified as the reduced or bypassed NDI and the simplistic motive is identified as "greed". Again, it should be noted that this string of latent root-causes typically spans many years and possibly different groups of individuals making it difficult, if not impossible, to pinpoint its origins. The "greed" simplistic explanation however, is readily accepted and after the obligatory hearings, firings and fines, 1D-NDI is mandated starting the vicious cycle all over again. The increased awareness is typically short-lived.

However, this approach treats the results of a problem and does not seek to identify and analyze the root-cause of the problem. Unless an excavator accidentally hits a pipeline for example, pipeline material deterioration occurs over time eventually leading to a failure. There is no single deterioration root-cause acting equally upon a 500 mile pipeline for example with some of it falling within the 1D-NDI detection dead-zones. Along the pipeline length, different deterioration root-causes may be acting upon the pipeline resulting in different deterioration rates, but 1D-NDI is inherently incapable of effectively identifying those root-causes as illustrated in FIGS. 2A and 2B. The objective of this invention to recognize features, including imperfections, is the first step in identifying the root-cause of material deterioration leading to effective failure preventive action.

Description of AutoFFS Computer

Figure 4:
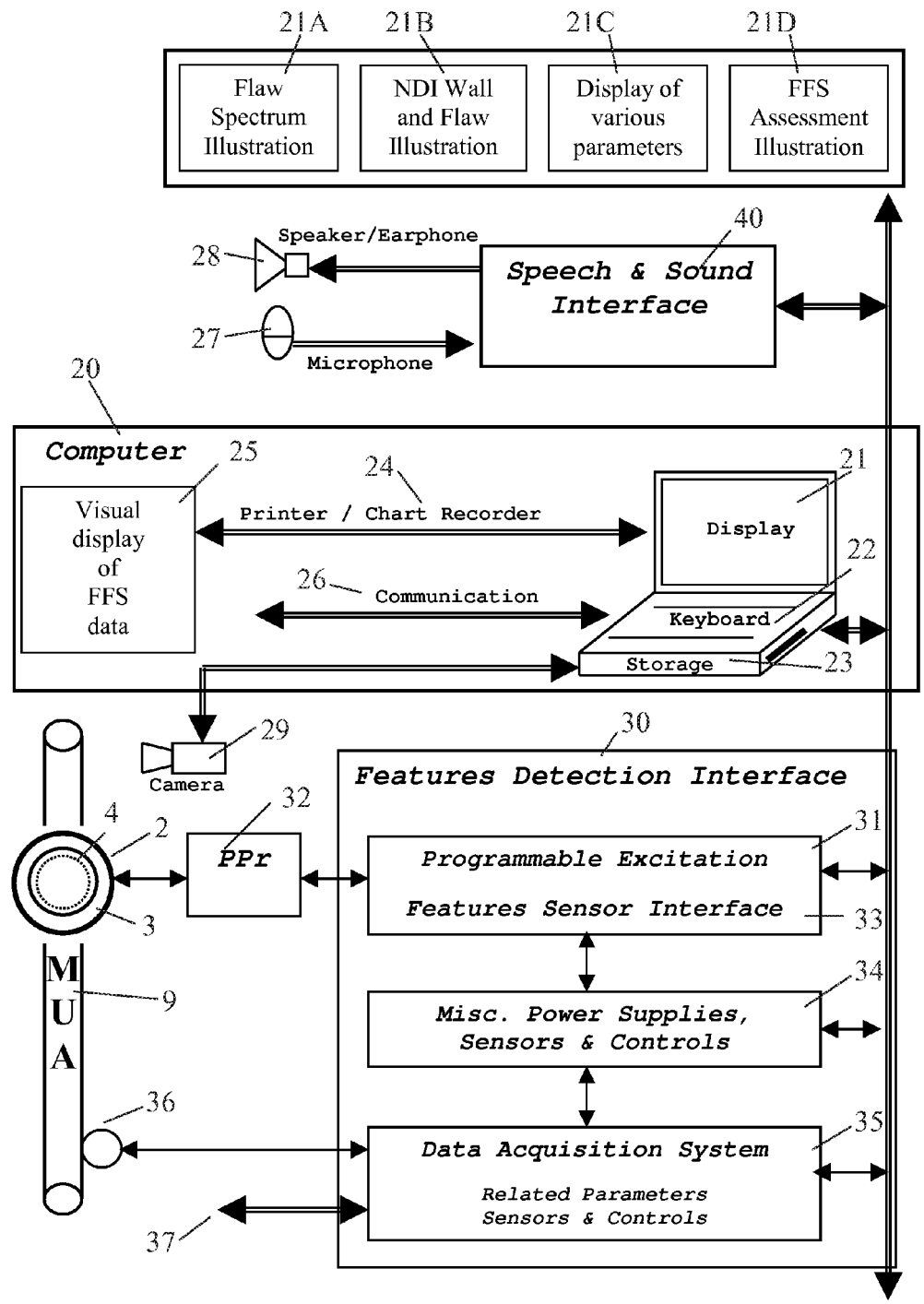
FIG. 4 illustrates a block diagram of the AutoFFS system according to the present invention.

FIG. 4 illustrates an AutoFFS block diagram further illustrating the computer 20, the features detection interface 30, the speech and sound interface 40 and the preferable information exchange among the components of the AutoFFS. It should be understood that the AutoFFS computer 20 may include more than just one computer such as a cluster of interconnected computers. It should be understood that the computer 20 does not necessarily comprise a laptop or portable personal computer and such misinterpretation should not be made from the illustrations in the figures and shall not be read as a limitation herein. The computer 20 preferably comprises a display 21, keyboard 22, storage 23, for storing and accessing data, a microphone 27, a speaker 28 and a camera 29. It should be understood that the display 21, the keyboard 22, the speaker 28 and the microphone 27 may be local to the computer 20, may be remote, may be portable, or any combination thereof. It should be further understood that camera 29 may comprise more than one camera. Further camera 29 may utilize visible light, infrared light, any other spectrum component, or any combination thereof. The camera 29 may be used to relay an image or a measurement such as a temperature measurement, a dimensional measurement (such as 3-G of the flaw spectrum), a comparative measurement, character and/or code recognition, such as a serial number, or any combination thereof including information to identify the MUA 9 and/or the authorized operator through biometric recognition. It should be appreciated that the storage 23 may comprise hard disks, floppy disks, compact discs, magnetic tapes, DVDs, memory, and other storage devices. The computer 20 may transmit and receive data through at least one communication link 26 and may send data to a printer or chart recorder 24 for further visual confirmation of the inspection data 25 and other related information. It should be understood that communication link 26 may be in communication through wired or wireless means, including but not limited to RFID, optical links, satellite, radio and other communication devices. At least one communication link 26 may facilitate communication with an expert in a remote location or an identification tag, such as RFID, embedded in MUA 9. Such embedded identification tags are described in U.S. Pat. No. 4,698,631, No. 5,202,680, No. 6,480,811 and No. 7,159,654 and are commercially available from multiple sources. The computer 20 preferably provides for data exchange with the features detection interface 30 and the speech and sound interface 40.

Speech and Voice Control

Speech is a tool which allows communication while keeping one's hands free and one's attention focused on an elaborate task, thus, adding a natural speech interface to the AutoFFS would preferably enable the operator to focus on the MUA 9 and other related activities while maintaining full control of the AutoFFS. Furthermore, the AutoFFS natural speech interaction preferably allows the operator to operate the AutoFFS while wearing gloves or with dirty hands as he/she will not need to constantly physically manipulate the system. Although various types of voice interaction are known in the art, many problems still exist in an industrial setting due to the potential of an excessive noise environment. Thus, this invention preferably provides for natural speech interaction between the human operator and the AutoFFS capable of deployment under adverse conditions.

Figures 8A, 8B, 8C, 8D:
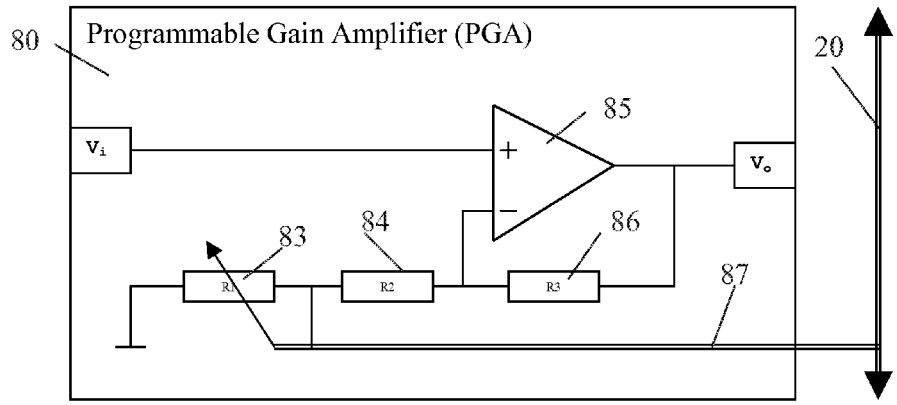
FIG. 8A illustrates a programmable gain amplifier according to the present invention.
FIG. 8B illustrates the design mathematical formula for the programmable gain amplifier of FIG. 8A according to the present invention.
FIG. 8C illustrates on possible example of values of components of the programmable gain amplifier in accord with the present invention.
FIG. 8D illustrates another possible example of values of components of the programmable gain amplifier in accord with the present invention.

FIG. 5 illustrates a block diagram of the AutoFFS system and the natural speech and sound interface 40 according to the present invention. Preferably, a natural speech command is received by the microphone 27 or other sound receiving device. The received sound is preferably amplified, such as by the amplifier 72. Amplifier 72 may be a programmable gain amplifier 80 as depicted in FIG. 8A. A feature of the embodiment is that the microphone amplifier 72 is followed by a bank of band-reject notch filters 71. Preferably, the operator and/or the software can adjust the amplifier 72 gain and the center frequency of the notch filters 71. Such a notch filter may be constructed by moving the low-pass filter 90 of FIG. 9A to the output 108 of the high-pass filter 100 of FIG. 10A. Since industrial noise is primarily machine generated, it typically consists of a single frequency and its harmonics. Therefore, adjustable notch filters 71 are well suited for the rejection of industrial noise. The notch filters 71 are preferably followed by the speech and sound recognition engine 70. The data from the speech and sound recognition engine 70 is preferably exchanged with the computer 20. Data from the computer 20 may be received by a sound synthesizer 50 and a speech synthesizer 60. The data received by the speech synthesizer 60 is converted into natural speech and is preferably broadcast through a speaker 28 It should be understood that each synthesizer may be connected to a separate speaker or multiple speakers and that in a different embodiment the speech synthesizer 60 and the sound synthesizer 50 may be integrated into a single function, the speech and sound synthesizer.

AutoFFS may be deployed on location, such as a wellsite, a chemical plant or refinery, an airport tarmac or a bridge, a storage yard or facility, a manufacturing facility, such as a pipe mill, a locomotive and in general in a noisy industrial and/or transportation environment. AutoFFS rarely is deployed in a laboratory where typical sound levels, similar to a bank lobby, may be in the range of 40 db to 50 db while factory or industrial sound levels may exceed 80 db. A frequency bandwidth of substantially 300 Hz to 2500 Hz and a dynamic range of substantially 40 db may be adequate for good quality speech with good quality listenability and intelligibility. Industrial noise may also be present in the same frequency range. The notch filters 71 may be "parked" outside of this frequency range or bypassed altogether when the noise level is acceptable. When a machine, a jet engine, or other device starts suddenly, the notch filters 71 would preferably sweep to match the predominant noise frequencies. The notch filters 71 may be activated either manually or through a fast tracking digital signal processing algorithm. Narrow notch filters 71 with a substantially 40 db rejection are known in the art and can thus be readily designed and implemented by those skilled in the art. Furthermore, it should be understood that standard noise cancellation techniques could also be applied to the output of the sound synthesizer 50 and the speech synthesizer 60 when the speaker 28 comprises a set of earphones such as in a headset.

Language Selection

It should be further understood that different AutoFFS may be programmed in different languages and/or with different commands but substantially performing the same overall function. The language capability of the AutoFFS may be configured to meet a wide variety of needs. Some examples of language capability, not to be viewed as limiting, may comprise recognizing speech in one language and responding in a different language; recognizing a change of language and responding in the changed language; providing manual language selection, which may include different input and response languages; providing automatic language selection based on pre-programmed instructions; simultaneously recognizing more than one language or simultaneously responding in more than one language; or any other desired combination therein. It should be understood that the multilanguage capability of the AutoFFS voice interaction is feasible because it is limited to a few dozen utterances as compared to commercial voice recognition systems with vocabularies in excess of 300,000 words per language.

Operator Identification and Security

Preferably, at least some degree of security and an assurance of safe operation, for the AutoFFS, is achieved by verifying the voiceprint of the operator and/or through facial or irisscan or fingerprint identification through camera 29 or any other biometric device. With voiceprint identification, the likelihood of a false command being carried out is minimized or substantially eliminated. It should be appreciated that similar to a fingerprint, an irisscan, or any other biometric, which can also be used for equipment security, a voiceprint identifies the unique characteristics of the operator's voice. Thus, the voiceprint coupled with passwords will preferably create a substantially secure and false command immune operating environment.

It should be further understood that the authorize operator may also be identified by plugging-in AutoFFS a memory storage device with identification information or even by a sequence of sounds and or melodies stored in a small playback device, such as a recorder or any combination of the above.

Assessment Trace to Sound Conversion

The prior art does not present any solution for the conversion of the assessment signals, including but not limited to inspection signals, also referred to as "assessment traces", to speech or sound. The present invention utilizes psychoacoustic principles and modeling to achieve this conversion and to drive the sound synthesizer 50 with the resulting sound being broadcast through the speaker 28 or a different speaker. Thus, the assessment signals may be listened to alone or in conjunction with the AutoFFS comments and are of sufficient amount and quality as to enable the operator to monitor and carry out the entire assessment process from a remote location, away from the AutoFFS console and the typical readout instruments. Furthermore, the audible feedback is selected to maximize the amount of information without overload or fatigue. This trace-to-sound conversion also addresses the dilemma of silence, which may occur when the AutoFFS has nothing to report. Typically, in such a case, the operator is not sure if the AutoFFS is silent due to the lack of features or if it is silent because it stopped operating. Furthermore, certain MUI 1 features such as, but not limited to, collars or welds can be observed visually and the synchronized audio response of the AutoFFS adds a degree of security to anyone listening. A wearable graphics display, such as an eyepiece, could serve as the remote display 21 to further enhance the process away from the AutoFFS console.

It should be understood that the assessment trace(s) to sound conversion is not similar to an annoying chime indicating that an automobile door is open, or that there is a message in an answering machine. The time varying AutoFFS processing results are converted to sound of sufficient amount and quality through psychoacoustic principles and modeling, as to enable the operator to monitor and carry out the entire AutoFFS process from a remote location without annoying the operator or resulting in operator overload or operator "zone-out". It should further be understood that a switch contact closure indicating that an automobile door is open or a vending machine bin is empty does not constitute an FFS assessment as it is not different than turning on the lights in a room. Conversely, a chime may be attached to the light to indicate that it is on or even a voice synthesizer to say "the light is on". Similarly, lights may be attached to a doorbell switch closure to assist a hearing impaired person, however, none of these devices or actions constitute an FFS assessment.

AutoFFS Speech

Text to speech is highly advanced and may be implemented without great difficulty. Preferably, when utilizing text to speech, the AutoFFS can readily recite its status utilizing, but not limited to, such phrases as: "magnetizer on"; "chart out of paper", and "low battery". It can recite the progress of the AutoFFS utilizing, but not limited to, such phrases as: "MUA stopped" and "four thousand feet down, six thousand to go". It can recite readings utilizing, but not limited to, such phrases as "wall loss", "ninety six", "loss of echo", "unfit material", "ouch", or other possible code words to indicate a rejectable defect. The operator would not even have to look at a watch as simple voice commands like "time" and "date" would preferably recite the AutoFFS clock and/or calendar utilizing, but not limited to, such phrases as "ten thirty two am", or "Monday April eleven".

However, it should be understood that the primary purpose of the AutoFFS is to relay MUA 9 information to the operator. Therefore, AutoFFS would first have to decide what information to relay to the operator and the related utterance structure.

AutoFFS Operation Through Speech

Preferably, the structure and length of AutoFFS utterance would be such as to conform with the latest findings of speech research and in particular in the area of speech, meaning and retention. It is anticipated that during the AutoFFS deployment, the operator would be distracted by other tasks and may not access and process the short term auditory memory in time to extract a meaning. Humans tend to better retain information at the beginning of an utterance (primacy) and at the end of the utterance (recency) and therefore the AutoFFS speech will be structured as such. Often, the operator may need to focus and listen to another crew member, an alarm, a broadcasted message or even an unfamiliar sound and therefore the operator may mute any AutoFFS speech output immediately with a button or with the command "mute" and enable the speech output with the command "speak".

The "repeat" command may be invoked at any time to repeat an AutoFFS utterance, even when speech is in progress. Occasionally, the "repeat" command may be invoked because the operator failed to understand a message and therefore, "repeat" actually means "clarify" or "explain". Merely repeating the exact same message again would probably not result in better understanding, occasionally due to the brick-wall effect. Preferably, AutoFFS, after the first repeat, would change slightly the structure of the last utterance although the new utterance may not contain any new information, a strategy to work around communication obstacles. Furthermore, subsequent "repeat" commands may invoke the help menu to explain the meaning of the particular utterance in greater detail.

The operator may remain in communication with the AutoFFS in a variety of conventional ways. Several examples, which are not intended as limiting, of possible ways of such communication are: being tethered to the AutoFFS; being connected to the AutoFFS through a network of sockets distributed throughout the site including the inspection head(s); being connected to the AutoFFS through an optical link (tethered or not); or being connected to the AutoFFS through a radio link. This frees the operator to move around and focus his/her attention wherever needed without interfering with the production rate.

It should be appreciated that the present invention may be a small scale speech recognition system specifically designed to verify the identity of the authorized operator, to recognize commands under adverse conditions, to aid the operator in this interaction, to act according to the commands in a substantially safe fashion, and to keep the operator informed of the actions, the progress, and the status of the AutoFFS process.

AutoFFS Sound Recognition

AutoFFS would preferably be deployed in the MUA 9 use site and would be exposed to the site familiar and unfamiliar sounds. For example, a familiar sound may originate from the rig engine revving-up to trip an OCTG string out of a well. An indication of the MUA 9 speed of travel may be derived from the rig engine sound. An unfamiliar sound, for example, would originate from an injector head bearing about to fail. It should be noted that not all site sounds fall within the human hearing range but may certainly fall within the AutoFFS analysis range when the AutoFFS is equipped with appropriate microphone(s) 27. It should also be noted that an equipment unexpected failure may affect adversely the MUA 9, thus training the AutoFFS to the site familiar, and when possible unfamiliar sounds, would be advantageous.

As discussed earlier, the notch filters 71 would preferably sweep to match the predominant noise frequencies, thus, a noise frequency spectrum may be derived that may further be processed for recognition using standard AutoFFS recognition techniques.

Description of Speech and Sound Interface

FIG. 6 illustrates a block diagram of a preferred sound synthesizer 50, speech synthesizer 60, and speech and sound recognition engine 70. It should be understood that these embodiments should not be viewed as limiting and may be tailored to specific inspection constraints and requirements.

The sound synthesizer 50 and the speech synthesizer 60 may comprise a tunes and notes table 51 and a vocabulary table 61 respectively. The digital-to-analog (herein after referred to as "D/A") converter 52, 62, the reconstruction filter 53, 63, and the variable gain output amplifier 54, 69 are iii communication with computer 20. The tunes and notes table 51 and a vocabulary table 61 may be implemented in a read only memory (ROM) or any other storage device. The computer 20 preferably sequences through the entire address sequence so that the complete digital data of the utterance (word, phrase, melody, tune, or sound), properly spaced in time, are converted to an analog signal through the D/A 52, 62. The analog signal is then preferably band-limited by the reconstruction filter 53, 63, amplified by the amplifier 54, 64, and sent to the speaker 28. Preferably, the computer 20 can vary the bandwidth of the reconstruction filter 53, 63 and adjust the gain of the amplifier 54, 64 which may be programmable gain amplifiers 80 as depicted in FIG. 8A. In a different embodiment, the gain of the amplifier 54, 64 may be adjusted by the operator.

It should be understood that the tunes and notes table 51 and a vocabulary table 61 may incorporate a built in sequencer with the computer 20 providing the starting address of the utterance (word, phrase, melody, tune, or sound). It should be further understood that the sound synthesizer 50 and the speech synthesizer 60 may comprise separate devices or even be combined into one device, the speech and sound synthesizer, or even be part of a complete sound and video system such devices being commercially available from suppliers such as YAMAHA. It should be understood that an utterance may comprise of a word, a short phrase and/or sound effects such as melodies, tunes and notes. A variable length of silence may be part of the utterance, which may or may not be part of the vocabulary table 61 and/or the tunes and notes table 51 in order to save storage space. Instead, the length of the silence may be coded in the table 51 and 61 and then be produced through a variable delay routine in computer 20.

The speech and sound recognition engine 70, may comprise an analog-to-digital (herein after referred to as "A/D") converter 73, a spectral analyzer 74, and the voice and sound templates table 75 which may be implemented in a read only memory (ROM) or any other storage device. The description of the sequence of software steps (math, processing, etc.) is well known in the art, such as can be found in Texas Instruments applications, and will not be described in detail herein. An exemplary hardware device is the YAMAHA part number 4MF743A40, which provides most of the building blocks for the entire system.

Voiceprint speaker verification is preferably carried out using a small template, of a few critical commands, and would preferably be a separate section of the templates table 75. Different speakers may implement different commands, all performing the same overall function. For example "start now" and "let's go" may be commands that carry out the same function, but are assigned to different speakers in order to enhance the speaker recognition success and improve security. As discussed herein above, code words can be used as commands. The commands would preferably be chosen to be multi-syllabic to reduce the likelihood of false triggers. Commands with 3 to 5 syllables are preferred but are not required. Further reduction of false triggers can be accomplished by a dual sequence of commands, such as "AutoFit" and upon a response from AutoFFS, such as "ready", followed by the actual command such as "Start" issued within a preset time interval. It should be understood that command pairs may or may not share trigger commands. Hardware trigger, such as a switch closure, followed by a speech command will be most effective in reducing false triggers.

Description of the Features Detection Interface

Computer 20 also controls and monitors a plurality of power supplies, sensors and controls 34 that facilitate the AutoFFS process including but not limited to MUA 9 identification and safety features. Further, computer 20 monitors/controls the data acquisition system 35 which preferably assimilates data from at least one sensor 36 and displays 21C and stores such data 23. The sensor 36 preferably provides data such as, but not limited to, MUA 9 location (feet of MUA 9 that passed through the head 2), penetration rate (speed of MUA 9 moving through the head 2), applied torque, rate of rotation (rpm), and coupling torque. It should be appreciated that the data to be acquired will vary with the specific type of MUA 9 and application and thus the same parameters are not always measured/detected. For example, the length of the MUA 9, such as a drill pipe joint, may be read from the MUA 9 identification markings or from the identification tag embedded in the MUA 9. Furthermore and in addition to the aforementioned techniques, computer 20 may also monitor, through the data acquisition system 35, parameters that are related to the assessment or utilization of the MUA 9 and/or parameters to facilitate FFS and/or remaining useful life estimation. Such parameters may include, but not be limited to, the MUA 9 pump pressure, external pressure, such as the wellhead pressure, temperature, flow rate, tension, weight, load distribution, fluid volume and pump rate and the like. Preferably, these parameters are measured or acquired through sensors and/or transducers mounted throughout the MUA 9 deployment area, such as a rig. For ease of understanding, these various sensors and transducers are designated with the numeral 37. The STYLWAN Rig Data Integration System (RDIS-10) is an example of such a hybrid system combining inspection and data acquisition. For instance, computer 20 may monitor, log and evaluate the overall drilling performance and its impact on the MUA 9 by measuring the power consumption of the drilling process, the string weight, weight on bit, applied torque, penetration rate and other related parameters. Such information, an indication of the strata and the efficiency of the drilling process, may be processed and used as a measure to further evaluate the MUA 9 imperfections and its FFS and/or remaining useful life.

It should be understood that sensors, measuring devices and/or a data acquisition system may already be installed in the MUA 9 deployment area, such as a drilling rig, measuring at least some of the aforementioned parameters, which may be available to AutoFFS through storage devices and/or through a communication link 26 as real time data and/or as historical data.

It should be appreciated that the RDIS-10 uses the extraction matrix and multidimensional sensors 4. When however, the multidimensional sensors and extraction matrix are replaced with a different sensor interface and a bank of frequency filters, as described herein below, the RDIS-10 will substantially work as described herein below utilizing the frequency derived flaw spectrum.

Regardless of the specific technique utilized, the AutoFFS device will preferably scan the material after each use, fuse the features data with relevant material use parameters, and automatically determine the MUA 9 status. Thus, a function of the features detection interface 30 is to generate and induce excitation 31 into the MUA 9 and detect the response, of the MUA 9, to the excitation 31. Preferably, at least one assessment head 2 is mounted on or inserted in the MUA 9 and the head 2 may be stationary or travel along the MUA 9. It should be appreciated that the head 2 can be applied to the inside as well as the outside of the MUA 9. It should be understood that the head 2, illustrated herein, may comprise at least one excitation inducer 3 and one or more features sensors 4 mounted such that the FFS assessment needs of MUA 9 are substantially covered. For features acquisition utilizing MFL, the excitation inducer 3 typically comprises of at least one magnetizing coil and/or at least one permanent magnet while sensor 4 comprises of sensors that respond to magnetic field. There is a plethora of sensors that respond to the magnetic field such as coils, Hall-probes, magneto diodes, etc. The computer 20 preferably both programs and controls the excitation 31 and the head 2 as well as receives features data from the head sensors 4 through the features sensor interface 33. The head 2, excitation 31, and the features sensor interface 33 may be combined within the same physical housing. In an alternative embodiment, the features sensors 4 may comprise computer capability and memory storage and thus the sensors 4 can be programmed to perform many of the tasks of the computer 20 or perform functions in tandem with the computer 20. It should be also understood that the application of the excitation 31 and the assessment of the MUA 9 may be delayed such as AutoFFS utilizing far-field or the residual magnetic field whereby the MUA 9 is magnetized and it is scanned at a later time, thus the excitation inducer 3 and the features sensor 4 may be mounted in different physical housings. It should be further understood, that in such configuration, the excitation inducer 3 may be applied on the inside or on the outside of MUA 9 while the inspection sensor 4 may be applied on the same side or on the opposite side of the excitation inducer 3. It should be further understood that either or both the excitation inducer 3 and the features sensor 4 may be applied on both the inside and on the outside of MUA 9 so that the assessment needs of MUA 9 are substantially covered.

Sensor Signal Processing

Preferably, the head 2 relates time-varying continuous (analog) signals, such as, but not limited to, echo, reluctance, resistance, impedance, absorption, attenuation, or physical parameters that may or may not represent a feature of the MUA 9. For features acquisition utilizing MFL, head 2 relates reluctance signals in an analog form. The processing of Eddy-Current amplitude and phase would also result in similar analog signal. Features generally comprise all received signals and may include MUA 9 design features such as tapers, imperfections, major and minor defects or other MUA 9 conditions such as surface roughness, hardness changes, composition changes, scale, dirt, and the like. Signals from three-dimensional sensors 4 are processed by the extraction matrix, that was published in 1994 and it is beyond the scope of this patent. The exemplary RDIS-10 uses the extraction matrix to decompose the converted digital signals into relevant features.

Typically, those in the 1D-NDI art have always relied on both an inspector and a manual verification crew for the interpretation of the inspection signals and any subsequent disposition of the MUI 1. However, based on extensive strength-of-materials knowledge, it is well known that the severity of an MUI 1 imperfection is a function of its geometry, its location, and the applied loads. It is also well known, in the art, that this information cannot be readily obtained by a verification crew when the imperfections in question are located underneath coating, in the near subsurface, in the mid wall, or in the internal surface of the MUI 1. Any destructive action, such as removing any coating or cutting up the MUI 1 is beyond the scope of non-destructive inspection. Detailed signal analysis can extract the pertinent information from the NDI signals. Preferably, such detailed signal analysis would utilize signals that are continuously related in form, kind, space, and time.

AutoFFS Retrofit to 1D-NDI Equipment

As discussed earlier, it is desirable to provide means to retrofit AutoFFS to the hundreds of 1D-EMI units deployed worldwide. The analog signals from 1D-NDI or two-dimensional sensors are decomposed in frequency. This frequency decomposition can take place in continuous or discrete form. In the continuous form the signals are decomposed through a bank of analog frequency filters and they are then digitized by the computer 20. In the discrete form the signals are digitized by the computer 20 and they are then decomposed through a bank of digital frequency filters or mathematical transforms.

The list of 1D-NDI retrofit candidates includes, but is certainly not limited to, the OCTG inspection units described in U.S. Pat. No. 2,685,672, No. 2,881,386, No. 5,671,155, No. 5,914,596 and No. 6,580,268; the pipeline pigs described in U.S. Pat. No. 3,225,293, No. 3,238,448 and No. 6,847,207 and the rail inspection systems described in U.S. Pat. No. 2,317,721, No. 5,970,438 and No. 6,594,591 and derived or similar units. The simplest retrofit would store the sensor information in a memory or transmit the sensor information through a communication link and the AutoFFS would post-process the data. The retrofit may consist of three-dimensional sensors and signal processing or frequency decomposition and signal processing as described herein below.

Frequency Decomposition with Analog Filters

FIG. 7 illustrates a block-diagram of the addition to the exemplary RDIS-10 imperfection sensor interface 33, illustrated as preprocessor 32, and the filter arrangement to decompose the inspection signals frequency spectrum and extract relevant features in an analog format. The features extraction of the present invention is accomplished through a filter bank comprising of a low-pass filter 90 and a number of band-pass filters 100 through 160N. There is no limit on the number of band-pass filters that may be used, however six to eight filters are adequate for most applications thus dividing the sensor frequency spectrum into seven to nine features, the exact number depending on the specific application. For a scanning speed of 60 feet/minute a typical alignment time shift (also known as time delay) is 42 milliseconds and a typical nine filter sequence comprises one 12 Hz low-pass filter 90 and eight band-pass filters 100 through 100N with center frequency (bandwidth) of 15 Hz (6 Hz), 25 Hz (10 Hz), 35 Hz (15 Hz), 50 HZ (21 Hz), 70 Hz (30 Hz), 100 Hz (42 Hz), 140 Hz (58 Hz) and 200 Hz (82 Hz). The attenuation of the filters depends on the resolution of the analog-to-digital converter and the processing with 40 to 60 decibels been sufficient for common applications.

The passband ripple is another important filter consideration. In the past, the 1D-EMI industry has mostly used Butterworth (also known as maximally-flat) filters. These are compromise filters with a 3 db passband variation. For typical 1D-NDI applications, better performance is achieved with Chebyshev or Elliptic filters. For example, a 0.5 db Chebyshev filter has less passband variation and sharper rolloff, thus resulting in a lower order filter than an equivalent Butterworth. The above specifications (filter type, center frequency, bandwidth and attenuation) are sufficient to design the filters without additional experimentation. Filter design software, some available free of charge, is also available from multiple component vendors such as, MicroChip, Linear Technology, and many others.

Preferably, the computer 20 may read and gather relevant sensor 4 information from the sensor 4 onboard memory and may write new information into the sensor 4 onboard memory. It should be understood that the sensor 4 relevant information may also be stored in other storage media, such as hard disks, floppy disks, compact discs, magnetic tapes, DVDs, memory, and other storage devices that computer 20 may access. The sensor 4 analog signal 4A is amplified by a programmable gain amplifier (herein after referred to as "PGA") 80. This Gain of the PGA 80 is controlled by the computer 20. FIG. 8A through 8D illustrate a PGA 80 and its design equations for clarity. PGAs are well known in the art and multiple designs can be found throughout the literature. PGA integrated circuits are also commercially available from such vendors as Analog Devices, Linear Technology, Maxim, National Semiconductors, Texas Instruments, and many others. In its simplest form a PGA comprises a differential amplifier 851 with a variable resistor 83 inserted in its feedback loop. Preferably, the variable resistor 83 is a digitally controlled potentiometer such as the ones offered by XICOR. Computer 20 may vary the variable resistor 83 value thus adjusting the gain of the PGA 80. The PGA 80 gain adjustment is primarily controlled by the sensor 4 information, the instantaneous scanning speed derived by the computer 20 from sensor 36 and the specific MUI 1. The output of PGA 80 is connected to a filter bank in order to decompose the inspection signals frequency spectrum and extract relevant features.

Figures 9A, 9B, 9C:
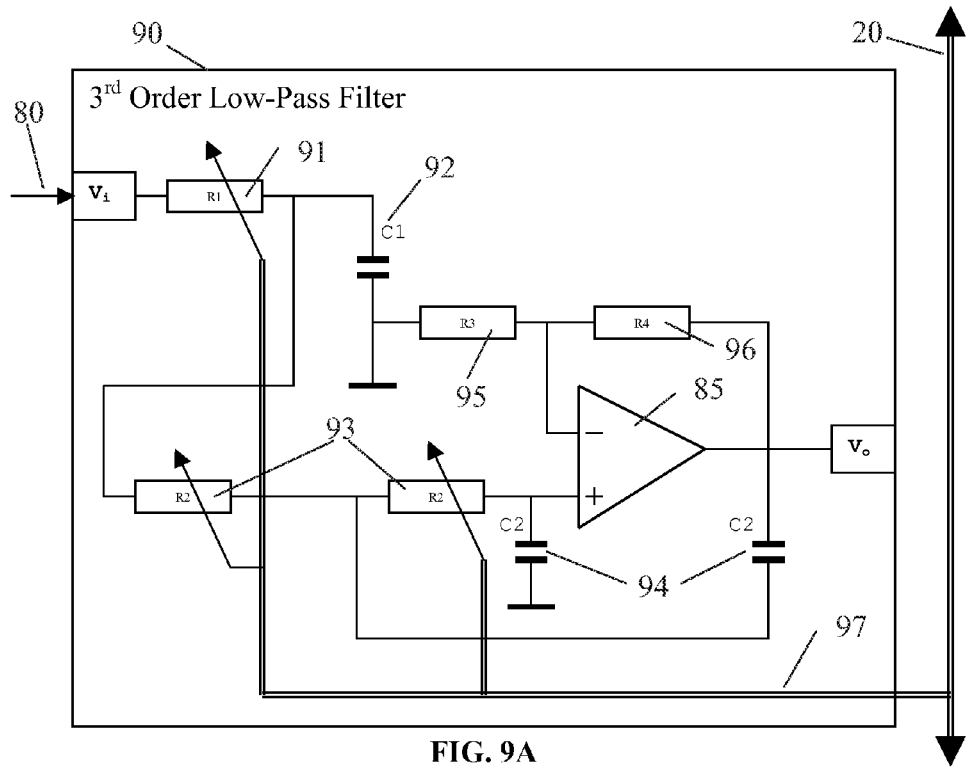
FIG. 9A illustrates a programmable $3^{rd}$ order low-pass filter according to the present invention.
FIG. 9B illustrates the design mathematical formula for a $1^{st}$ order low pass filter of FIG. 9A according to the present invention.
FIG. 9C illustrates the design mathematical formula for a $2^{nd}$ order low pass filter of FIG. 9A according to the present invention.

The low frequency components are extracted by the low-pass filter 90. It should be understood that the term low-frequency features are not in absolute terms but in relative terms to the scanning speed. Therefore, the cutoff frequency of the low-pass filter 90, denoted as Fc in FIGS. 9B and 9C, may be set to 5 Hz for one scanning speed and to 50 Hz for a higher scanning speed. The exact cutoff frequency of the low-pass filter 90 depends on the sensor information 4, the instantaneous scanning speed derived by the computer 20 from sensor 36, and the specific MUI 1. FIGS. 9A, 9B and 9C illustrate a programmable $3^{rd}$ order low-pass analog filter and its design equations for clarity. Low-pass filters are well known in the art and their design can be found throughout the literature. Filter design software, some available free of charge, is also available from multiple component vendors such as, MicroChip, Linear Technology, and many others. The low-pass filter of FIG. 9A consists of two sections. A $1^{st}$ order filter comprising of resistor 91 and capacitor 92 cascaded with a $2^{nd}$ order low-pass analog filter. It should be understood that all other filter orders can be obtained by cascading additional filter sections. Preferably, the variable resistors 91 and 93 are digitally controlled potentiometers such as the ones offered by XICOR and a fixed resistor value (not shown) similar to the FIG. 8A network 83 and 84. Computer 20 may vary the variable resistor 91 and 93 value thus adjusting the cutoff frequency of the low-pass filter.

Figures 10A, 10B, 10C:
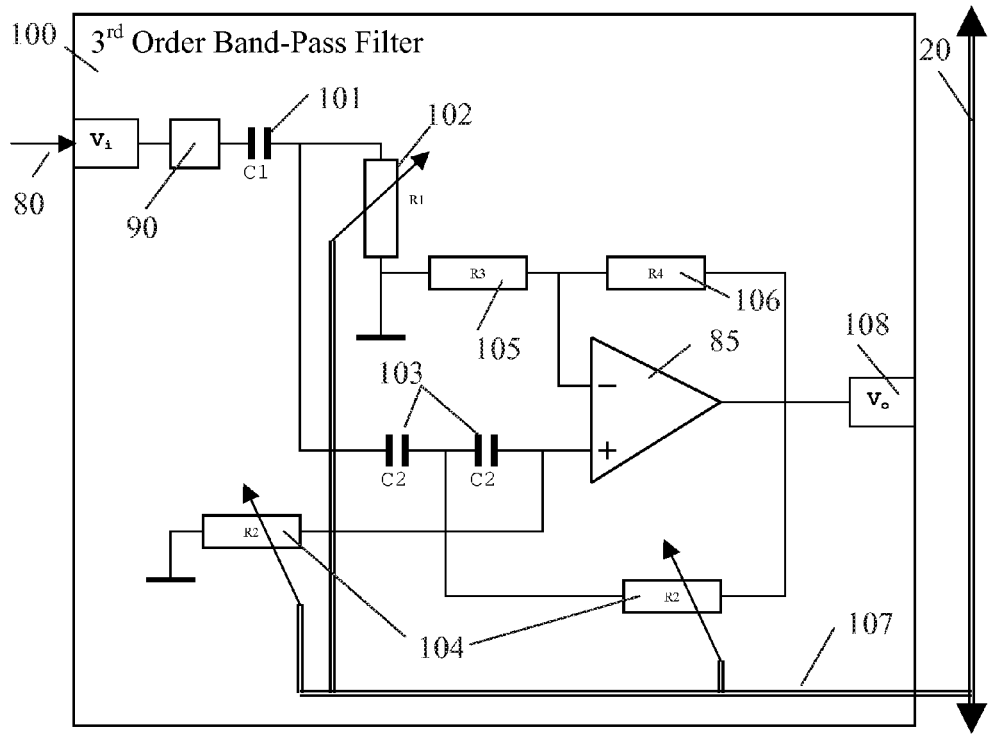
FIG. 10A illustrates a programmable band-pass filter and a $3^{rd}$ order high-pass filter according to the present invention.
FIG. 10B illustrates the design mathematical formula for a $1^{st}$ order high-pass filter of FIG. 10A according to the present invention.
FIG. 10C illustrates the design mathematical formula for a $2^{nd}$ order high-pass filter of FIG. 10A according to the present invention.

All other frequency components of the sensor signal 4 are extracted by the band-pass filters 100 through 100N. Again, it should be understood that the frequency bands are not stated in absolute terms but in relative terms to the scanning speed. Therefore, the center frequency of a band-pass filter 100 may be set to 40 Hz for one scanning speed and to 200 Hz for a higher scanning speed. The exact center frequency of the band-pass filters 100 through 100N depends on the sensor information 4, the instantaneous scanning speed derived by the computer 20 from sensor 36 and the specific MUI 1. FIG. 10A illustrates a programmable $3^{rd}$ order band-pass filter that is made up from a low-pass filter 90 cascaded with a $3^{rd}$ order high-pass filter. The $3^{rd}$ order high-pass filter and its design equations are shown for clarity. High-pass filters are well known in the art and its design can be found throughout the literature. Filter design software, some available free of charge, is also available from multiple component vendors such as, MicroChip, Linear Technology, and many others. The high-pass filter of FIG. 10A includes two sections. A $1^{st}$ order filter comprising of capacitor 101 and resistor 102 cascaded with a $2^{nd}$ order high-pass filter. It should be understood that all other filter orders can be obtained by cascading additional filter sections. Preferably, the variable resistors 102 and 104 are digitally controlled potentiometers such as the ones offered by XICOR and a fixed resistor value (not shown) similar to the FIG. 8A network 83 and 84. Computer 20 may vary the variable resistor 102 and 104 value thus adjusting the cutoff frequency of the high-pass filter. It should be further understood that this band-pass filter configuration allows for individual adjustment of both the leading and trailing transition bands. Other band-pass filter configurations can also be found throughout the literature.

Frequency Decomposition in the Digital Domain

The features extraction filter bank that was described above using analog filters, may also be realized with switched capacitor filters and/or digital filters and/or mathematical transforms or any combination thereof. Switched capacitor filters may be substituted for the analog filters 90 and 100 through 100N with the computer 20 varying the clock frequency to program the resulting switched capacitor filter bank.

It should be understood that no modification to the front end of the inspection sensor interface 33 (i.e. no preprocessor 32 as described hereinabove) of the exemplary RDIS-10 is required in order to implement the present invention using digital filters and/or mathematical transforms as the exemplary RDIS-10 is designed for digital domain operation.

The sensor signal therefore, is converted to digital format and the analog filters described above may be converted to their digital counterpart using bilinear transform which is well known to the art and well publicized resulting in Infinite Impulse Response digital filters (known to the art as IIR filters) and is illustrated in FIGS. 11A, 11B and 11C. The block diagram of FIG. 7 may then be used to derive the flowchart of the digital signal processing form of the present invention. In another implementation, digital filters may be designed using direct synthesis techniques that are also well known to the art and well publicized. Finite Impulse Response digital filters (known to the art as FIR filters) may also be employed at the expense of computing power. FIR implementations, such as Kaiser, Hamming, Hanning etc, are also well known to the art and well publicized.

There are many mathematical transforms that are well known and well publicized. However, not all are useful for features extraction for the transient NDI signals. The NDI industry in the past has proposed the use of Fourier Transform or its Fast Fourier Transform (FFT) implementation, a misapplication for the brief transient NDI imperfection signals. Fourier Transform, in all of its implementations, is useful to analyze long periodic signals (long waves). Furthermore, the Fourier Transform provides information in the frequency domain and none in the time domain which is essential for the analysis of NDI signals. This drawback of the Fourier Transform was noted by the French Academy and in particular by J. L. Lagrange who objected to the Fourier Transform trigonometric series because it could not represent signals with corners such as the ones often encountered in NDI. Subsequently, the Academy refused to publish the Fourier paper. In order to overcome the drawbacks of the Fourier Transform, alternatives were developed over the years, notably the Short Time Fourier Transform (commonly referred to as STFT), wavelets and coiflets all of which are well known to the art and well publicized. The main disadvantages of the transforms are their fixed resolution and their demand for higher computer power.

The STFT offers uniform time and frequency resolution throughout the entire time-frequency domain using a fixed window size, which results in its main drawback. A small window blind the STFT to low frequencies while a large window blinds the STFT to brief signal changes mostly associated with use induced MUI 1 imperfections.

Wavelets (short waves) are better tuned to the needs of NDI. Wavelets vary the width of the window thus offer better time resolution for the higher frequencies that are typically associated with use induced MUI 1 imperfections. Wavelets are typically implemented using filter banks and they are also well known in the art and well publicized. FIGS. 12A, 12B and 12C illustrate the implementation of the discrete wavelet transform decomposition using filter banks and downsampling.

Sensor Signal Normalization

Referring back to FIG. 7, the bank of PGAs 80A through 80N follows the frequency decomposition filter bank. The frequency response of the inspection sensors 4 is typically non-linear. The response of the inspection sensor 4 to the same MUI 1 feature would then vary depending on the scanning speed and level of excitation which is continuously monitored by computer 20. The sensor 4 response to different scanning speeds, in the unique setting of the inspection head 2 under varying excitation 31 levels, can be characterized. This is accomplished by scanning MUI 1 samples with test imperfections at different speeds and different levels of excitation while recording the sensor 4 signals. Preferably, these sensor characterization tests would be repeated multiple times so that a sufficiently large database for the specific sensor is obtained. The characteristics of the particular sensor 4 are then preferably stored in the memory onboard the sensor 4. Computer 20 reads the sensor 4 characteristics and adjusts the bank of PGAs 80A through 80N to normalize the sensor signal. This band signal amplitude compensation along with the capability of computer 20 to adjust both the pass-band width and the transition slopes of the filters allows computer 20 to fully normalize the imperfection signals.

The outputs of the bank of PGAs 80A through 80N are then converted to digital form through an analog-to-digital converter of sufficient resolution, typically 10 to 14 bits, and speed which is defined by the number of channels and maximum scanning speed.

AutoFFS Processing

AutoFFS processing operates upon the flaw spectrum that was derived from signals, such as, but not limited to, echo, reluctance, resistance, impedance, absorption, attenuation, sound or physical parameters acquired through one-dimensional or multi-dimensional sensors. The processing of Eddy-Current amplitude and phase, for example, may also be utilized to derive the flaw spectrum as well as frequency decomposition as described herein above. Regardless of the signal origin or the frequency decomposition method used, the frequency components of the signals then become the flaw spectrum for use by the AutoFFS in a manner illustrated by element 21A in FIG. 13. It should be understood that computer 20 can manipulate and present the signals in any desirable format. It should be further understood that the signals of geometrically offset sensors, such as the ones shown in FIG. 7 of U.S. Pat. No. 2,881,386, are aligned by computer 20 through time shifting (time delay) primarily controlled by the scanning speed preferably derived from sensor 36. This may comprise memory, a bucket-brigade, or any combination of the above. Variable length analog delay lines may also be deployed, the delay length controlled primarily by the scanning speed. It should be understood that sensor 36 may comprise a number of sensors distributed along the length of MUI 1 for direct measurement or coupled to MUI 1 transport components, such as the lifting cable, or a combination thereof.

It should be understood that the exemplary RDIS-10 extraction matrix is compiled through a software program, that was published in 1994 and it is beyond the scope of this patent, and decomposes the converted digital signals into relevant features. The extraction matrix may be adjusted to decompose the signals into as few as two (2) features, such as, but not limited to, the 1D-NDI presentation of wall and flaw. It should be understood that no theoretical decomposition upper limit exists, however, fifty (50) to two hundred (200) features are practical. The selection of the identifier equations, further described herein below, typically sets the number of features. In the exemplary RDIS-10, the decomposed signals, regardless of their origin, are known as the flaw spectrum 6 (see FIG. 2C).

Feature Recognition

Humans are highly adept in recognizing patterns, such as facial features or the flaw spectrum 6 and readily correlating any pertinent information. Therefore, it is easy for the inspector to draw conclusions about the MUI 1 by examining the flaw spectrum 6, as further illustrated in FIGS. 15A through 15E. During the inspection, the inspector further incorporates his/her knowledge about the MUI 1 present status, his/her observations, as well as the results of previous inspections. The success of this inspection strategy of course, solely depends on how well the inspector understands the flaw spectrum 6 data and the nuances it may encompass.

Computers can run numerical calculations rapidly but have no inherent pattern recognition or correlation abilities. Thus, a program has been developed that preferably derives at least one mathematical procedure to enable the computer 20 to automatically recognize the patterns and nuances encompassed in decomposed inspection and/or sound data streams such as presented in the flaw spectrum 6. The detailed mathematical procedures are described hereinbelow and enable one skilled in the art to implement the AutoFFS described herein without undue experimentation.

Figure 13:
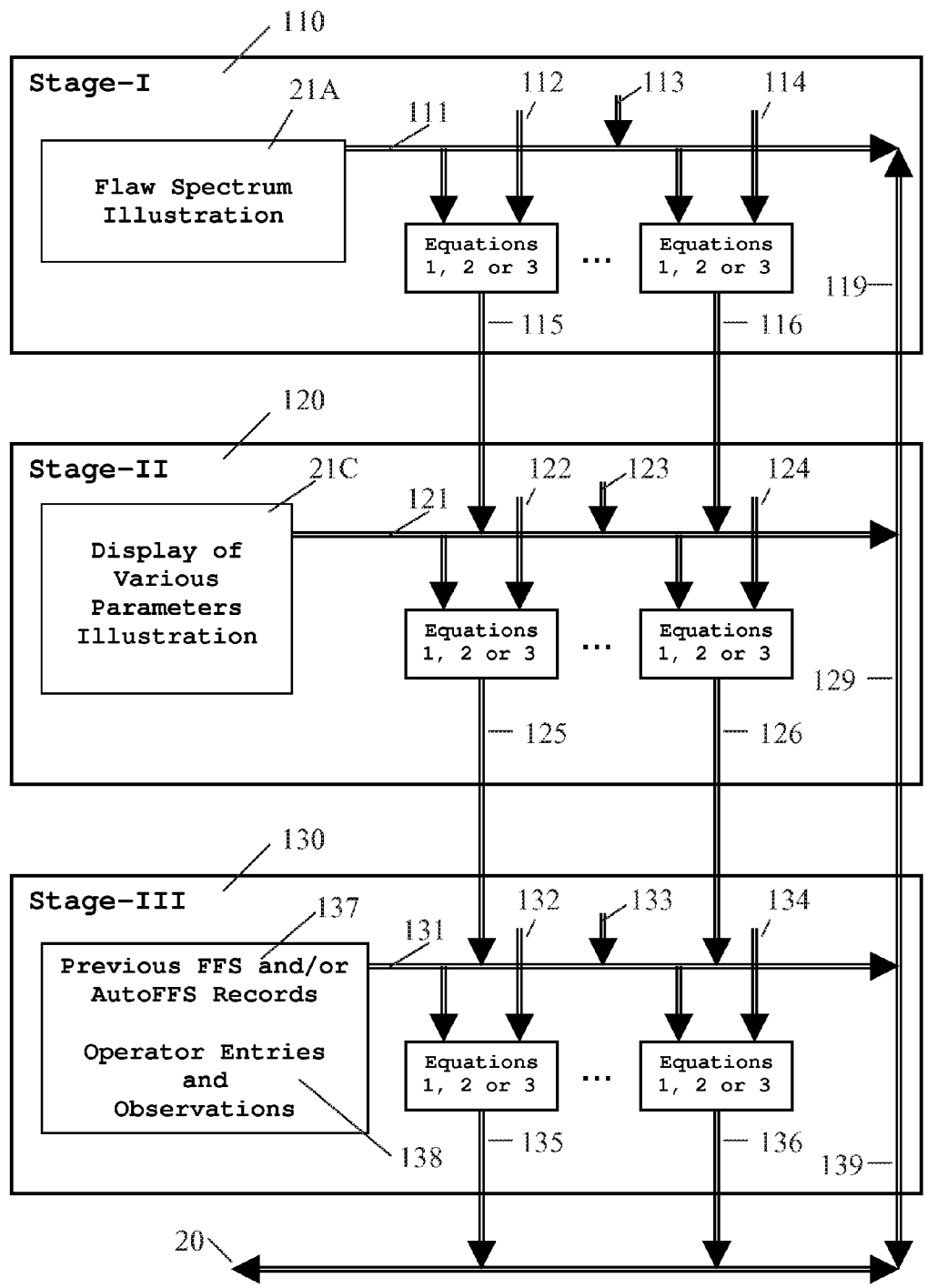
FIG. 13 illustrates a block diagram of the signal processing of AutoFFS system according to the present invention.

FIG. 13 illustrates a block diagram of an AutoFFS data processing sequence that allows the creation of a software flowchart and the translation of the practice to a computer program. For stand-alone operation, the AutoFFS must be optimal in regard to the FFS assessment criteria and application limitations, commonly defined by approximations and probabilities which are referred to herein as constraints. It should be understood therefore, that the AutoFFS state variables must be tuned for optimal performance under different constrains depending on the MUA 9 and its application. The fundamental operation of the AutoFFS is performed by the identifier equations which preferably capture the optimal mutual features in accordance to the constraints. It should be understood that a number of identifier equations may be paralleled and/or cascaded, each one utilizing a different set of optimal mutual features. Furthermore, it should be understood that the processing of the identifier equations may be carried out by a single computer 20 or by different computers in a cluster without effecting the overall result.

The first stage identifier equations, with elements denoted as $a_{jk}$ 112, 114, use for input N features 111 mostly derived from the flaw spectrum 21A. Additional features may be provided by fixed values referred to herein as bias 113, 123, 133. Bias may be a single constant or a sequence of constants that may be controlled, but not limited, by time or by the MUA 9 length. Backwards chaining 119 limits irrelevant processing and enhances stability while forward chaining 139 propagates features to later stages or it may inform computer 20 that an MUA 9 condition has been determined and no further analysis is required. It should be further understood that both forward and backward chaining may be direct, through memory, through a bucket-brigade, or any combination of the above. It should be further understood that all or any subsystem of the AutoFFS may be implemented as a casual system or as a non-casual system. In a casual implementation only past and present features 111 are utilized. In a non-casual implementation, features 111 are utilized through memory, through a bucket-brigade, or any combination of the above thus allowing for the use of future values of the features 111. Future values of the features 111 may be used directly or indirectly as signal masks and may be propagated through the forward chaining 139. Utilization of future values of features 111 increases the AutoFFS stability and reduces the probability of a conflict In Equations 1-3, shown below, such features are denoted as Xa. Based on the constrains, the identifier equations reduce the features 111 and bias 113 to identifiers 115, 116 denoted as Ya of the form:

$$Ya_{ij} = M \sum_{k=1}^{N} a_{ik} Xa_{kj} \qquad \text{(Equation 1)}$$

The identifiers Ya 115, 116 can be fed back through the backwards chaining 119, can be used directly through the forward chaining 139, can be used as variables to equations or as features 121, 131 in following stages or in their most practical form, as indexes to tables (arrays) which is shown in Equation 2 for clarity.

$$Ya_{ij} = M \left[ 1 + e^{-\sum_{k=1}^{K} a_{ik} Xa_{kj}} \right]^{-1} \qquad \text{(Equation 2)}$$

where T is a Look-up Table or Array.

Another useful identifier form is shown in Equation 3.

$$Ya_{ij} = T_{(M \sum_{k=1}^{N} a_{ik} Xa_{kj})} \qquad \text{(Equation 3)}$$

where M is a scaling constant or function.

It should be understood that each stage may comprise multiple identifier equations utilizing equations 1, 2, or 3. There is no theoretical upper limit for the number of identifiers calculated, however, five (5) to ten (10) identifiers are practical.

Some of the identifiers Ya 115, 116 may be sufficient to define the disposition of the MUI 1 alone and thus propagate to the output stage 139 while others may become features for the second stage 120 of identifier equations along with features 121 pertinent to the Ya identifiers, all denoted as Xb. It should be appreciated that in the exemplary STYLWAN RDIS-10, depending on the constrains, those features can be obtained from the operator interface, from the computer 20 memory, from the camera 29, or by connecting directly to the STYLWAN RDIS-10 Data Acquisition System transmitters that measure various parameters illustrated FIG. 41 (21C). Examples of such transmitters include the OCI-5000 series manufactured by OLYMPIC CONTROLS, Inc, Stafford, Tex., USA, such as transmitters that measure pressure (OCI- 5200 series), temperature (OCI-5300 series), speed and position (OCI-5400 series), weight (OCI-5200H series), fluid level (OCI-5200L series), flow (OCI-5600 series), dimensions (OCI-5400D series), AC parameters (OCI-5400 series), DC parameters (OCI-5800 series), as well as other desired parameters. The second stage 120 identifier equations, with elements denoted as produces identifiers 125,126 denoted as Yb of similar form as the Ya identifiers 115, 116.

Again, some of the identifiers Yb may be sufficient to define the disposition of the MUI 1 alone and thus propagate to the output stage 139 while others may become features for the third stage 130 identifier equations along with features pertinent to the Yb identifiers, all denoted as Xc. For the RDIS-10, depending on the constrains, those features can be obtained from data or functions entered by the operator 138, stored in historical data 137, or other predetermined sources (not illustrated). It should be understood that this process may repeat until an acceptable solution to the constraints is obtained, however, three stages are typically adequate for the exemplary STYLWAN RDIS-10. It should further be understood that each stage 110, 120 and 130 may comprise multiple internal stages.

Determination of Coefficients

For the determination of the $a_{ik}$ coefficients, the tuning of the identifier equations, a set of flaw spectrums 6 of known similar imperfections that are pertinent to a current inspection application are required. These data sets, of flaw spectrums 6, are referred to herein as baseline spectrums. Preferably, all the $a_{ik}$ coefficients are initially set equal. It should be understood that because this is an iterative process the initial values of the $a_{ik}$ coefficients could also be set by a random number generator, by an educated guess, or by other means for value setting.

Since the baseline spectrums are well known, typically comprising data taken for similar imperfections, the performance measure and the constrains are clearly evident and the coefficients solution is therefore objective, although the selection of the imperfections may be subjective. By altering the coefficient values through an iterative process while monitoring the output error an acceptable solution would be obtained.

There are multiple well-known techniques to minimize the error and most of these techniques are well adept for computer use. It should be appreciated that for the AutoFFS limited number of features a trial-and-error brute force solution is feasible with the available computer power. It should be further expected that different solutions would be obtained for every starting set of coefficients. Each solution is then evaluated across a variety of validation spectrum as each solution has its own unique characteristics. It is imperative, therefore, that an extensive library of both baseline spectrums and validation spectrums must be available for this evaluation. It should be further understood that the baseline spectrums cannot be used as validation spectrums and visa versa. Furthermore, it should be understood that more than one solution may be retained and used for redundancy, conflict resolution, and system stability. Still further in applications of the AutoFFS, the terms "acceptable" or "good enough" are terms of art to indicate that, in a computational manner, the computer has completed an adequate number of iterations to compile an answer/solution with a high probability of accuracy.

Once a set or sets of coefficients are obtained, the number of non-zero coefficients is preferably minimized in order to improve computational efficiency. This is important because each identifier equation is just a subsystem and even minor inefficiencies at the subsystem level could significantly affect the overall system real time performance. Multiple techniques can be used to minimize the number of non-zero coefficients. A hard threshold would set all coefficients below a predetermined set point to zero (0). Computers typically have a calculation quota, so a quota threshold would set to zero a sufficient number of lower value coefficients to meet the calculation quota. A soft threshold would subtract a non-zero constant from all coefficients and replace the negative values with zero (0). Since an error measure exists, the new set of coefficients can be evaluated, the identifier equations can be tuned again and the process could repeat until the admissible identifier equation is determined. It is preferred that multiple admissible identifier equations are determined for further use. It should be appreciated that although the preference for multiple admissible identifiers may appear to complicate potential resolutions, the use of computer power makes a large number of iterations feasible.

For the assessment of materials, an acceptable solution would always contain statistics based on false-positive and false-negative ratios. A false-positive classification rejects fit material while a false-negative classification accepts unfit material. Using more than one identifier equation lowers the false ratios more than the fine-tuning of a single identifier equation. It should be understood that this process theoretically provides an infinite number of solutions, as an exact formulation of the inspection problem is elusive and always based on constrains. Furthermore, for a solution that can be obtained with a set of coefficients, yet another solution that meets the performance measure may also be obtained by slightly adjusting some of the coefficients. However, within the first three to five proper iterations the useful solutions become obvious and gains from additional iterations are mostly insignificant and hard to justify.

Once all of the Stage-I 110 admissible identifier equations have been determined, their identifiers become features in Stage-II 120 along with the additional features 121, bias 123, and forward and backwards chaining 129. The starting set of baseline spectrums is then processed through the admissible identifier equations and the results are used to tune the Stage-II 120 identifier equations in a substantially identical process as the one described above for the Stage-I 110. The process repeats for the Stage-III 130 identifier equations and any other stages (not illustrated) that may be desired or necessary until all the admissible subsystems are determined and the overall system design is completed. It should be appreciated that in practice, preferably only two to five stages will be necessary to obtain required results. When the final coefficients for all of the equations are established, the overall system performance may be improved by further simplifying the equations using standard mathematical techniques.

A previous assessment with the same equipment provides the best historical data 137. The previous FFS assessment, denoted as $Ys_{(-1)}$, is ideally suited for use as a feature 131 in the current inspection as it was derived from substantially the same constrains. Furthermore, more than one previous FFS assessment 137 may be utilized. Features 131 may be backwards chained 129, 119. Multiple historical values may allow for predictions of the future state of the material and/or the establishment of a service and maintenance plan.

Determination of Bias

In conventional inspection systems, previous state data, that was derived through a different means under different constrains, could not necessarily be used directly or used at all. If utilized, the data would more likely have to be translated to fit the constrains of the current application. It should be appreciated that such a task may be very tedious and provide comparatively little payoff. For example, there is no known process to translate an X-Ray film into MFL pertinent data.

However, the AutoFFS system described herein allows for the use of such data in a simple and direct form. In the X-Ray example, the opinion of an X-Ray specialist may be solicited regarding the previous state of the material. The specialist may grade the previous state of the material in the range of one (1) to ten (10), with one (1) meaning undamaged new material. The X-Ray specialist opinion is an example of bias 113, 123, 133.

Bias 113, 123, 133 may not necessarily be derived in its entirety from the same source nor be fixed throughout the length of the material. For example, information from X-Rays may be used to establish the previous material status for the first 2,000 feet of an 11,000 foot coiled tubing string. Running-feet may be used to establish the previous material status for the remainder of the string except the 6,000 foot to 8,000 foot range where OD corrosion has been observed by the inspector 138. From the available information, the previous material status for this string (bias per 1,000 feet') may look like [2, 2, 4, 4, 4, 4, 7, 7, 4, 4, 4] based on length. Other constrains though may impose a hard threshold to reduce the bias into a single value, namely [7], for the entire string.

An example of a bias array would be a marine drilling riser string where each riser joint is assigned a bias based on its age, historical use, Kips, vortex induced vibration, operation in loop currents, visual inspection, and the like. The bias for a single riser joint may then look like [1, 1, 3, 1, 2, 2]. Identifier equations may also be used to reduce the bias array into a bias value or a threshold may reduce the bias into a single value.

Fitness for Service Assessment

AutoFFS provides means to move the FFS process from the laboratory or the engineering department to the field and apply FFS to the in-service material using actual as-is field data. Furthermore, it should be understood that AutoFFS may be utilized to gather actual filed data to create FFS methods, charts, tables and formulas or to verify the validity of proposed or existing FFS methods, charts, tables and formulas. AutoFFS may utilize industry standard or custom FFS methods, charts, tables and formulas, utilize original design data and criteria, material test reports, deployment history, prior inspection records, prior FFS records, repair and/or alteration records along with FFS assessment techniques and/or formulas and/or data sets, imperfection allowance rules and/or formulas and/or data sets, acceptance criteria, remediation options and/or formulas and/or data sets. AutoFFS makes provisions to accept such information/data either as a mathematical or logical (crisp or fuzzy) formula, as a sequence of data, such as bias, or even as a single constant.

Typically and in addition to FDDim, AutoFFS would evaluate material utilizing: a) absolute values, such as actual wall thickness; b) parameter ratios or remaining ratios, such as (strength of damaged material)/(strength of undamaged material); c) coverage ratios, such as (pitted area surface)/(material surface) and d) rates of change, such as feature morphology, size, density, coverage and any combination thereof. Preferably, AutoFFS would also utilize a measure of the damage mechanism time-dependency. AutoFFS would apply FFS assessment for each feature and/or damage mechanism and then fuse the results of each assessment to determine the status of the material. It should be understood that the combination of FDDim with the other AutoFFS measured/calculated values would result in a multidimensional pointer sufficient to select the material status from a multidimensional group of tables or charts or to solve a system of equations. For example, remaining wall thickness FFS tables and charts may be indexed on the (maximum) operating pressure and temperature. By continuously monitoring the actual operating pressure and temperature, AutoFFS would then select the appropriate FFS assessment path and alert the operator when operating pressure and temperature exceed a limit. In a different embodiment, AutoFFS could establish communication with a pressure and temperature monitor using communication port 26 and download the pressure and temperature historical data from the monitor memory. Such data may also be available in a storage device 23.

AutoFFS may also utilize the damage mechanism time-dependency for prognosis or prediction of the remaining useful life. Since AutoFFS would preferably be monitoring other controlling parameters, such as pressure, temperature, deflection etc, it should be understood that AutoFFS prognosis and/or predictions would be based on measured parameters instead of estimated parameters. It should be further understood that even small changes in the application and/or environment might result in significant FFS changes. Therefore, any AutoFFS prognosis or prediction would be bound by the monitored stability of the controlling parameters. AutoFFS preferably may a) scan the MUA 9 after each use; b) identify the features of MUA 9; c) quantify the features of MUA 9; d) assess the impact of the features upon the MUA 9, e) determine the FFS of MUA 9 under the constraints of the application and f) (optional) generate and export a file for use by an FEA engine. It should also be apparent that AutoFFS deployment and utilization should be economically sound.

Figure 14:
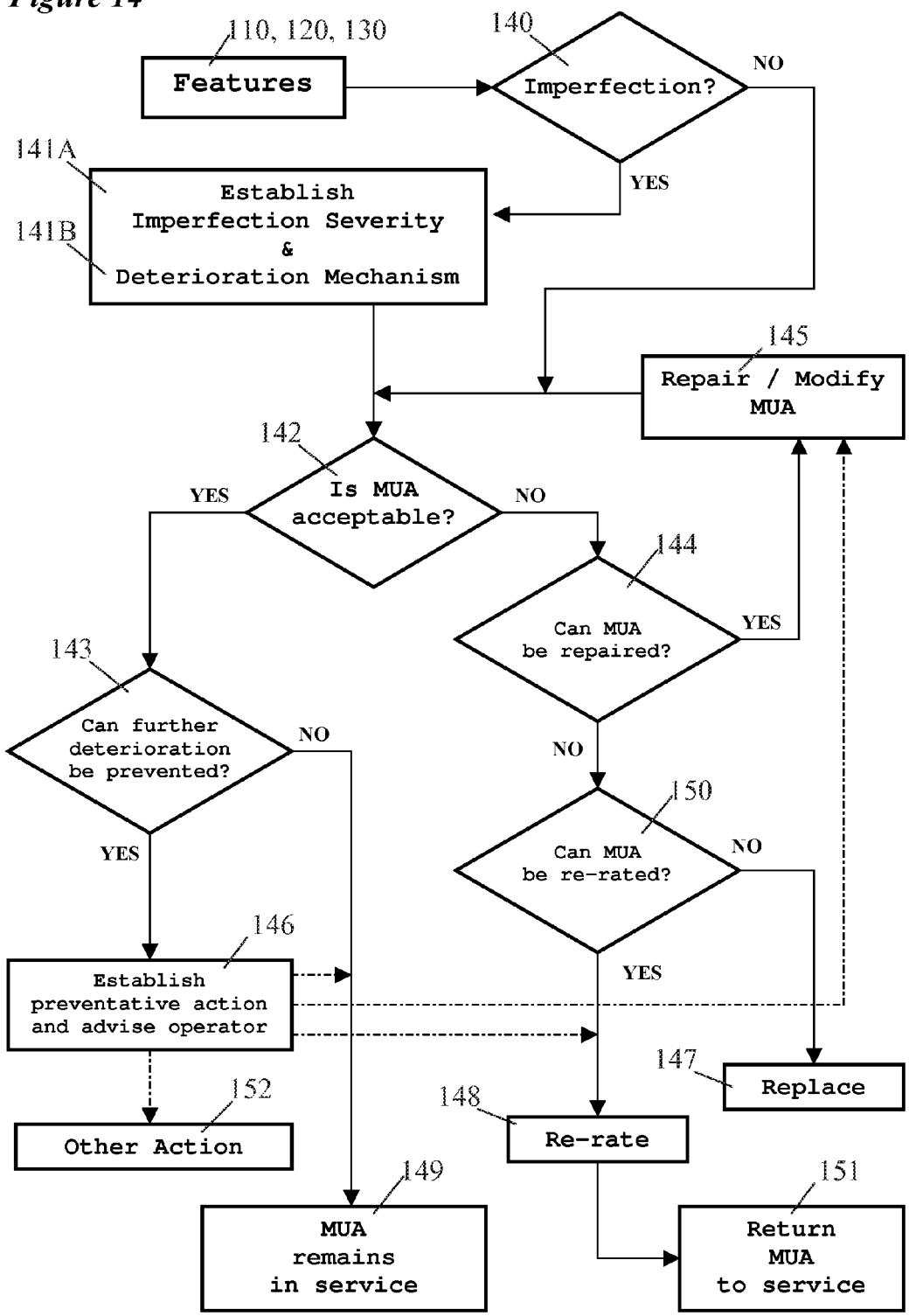
FIG. 14 illustrates a flow chart of a typical FFS assessment according to the present invention.
Figure 15A:
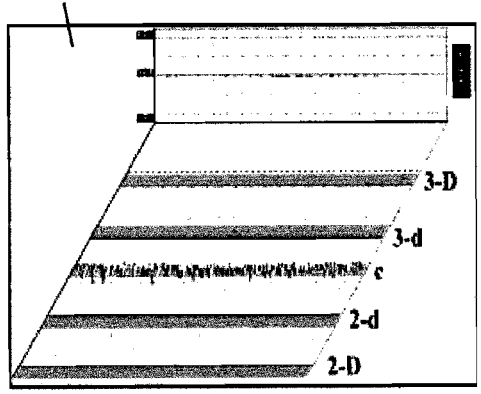
FIG. 15A shows a flaw spectrum of a new coil in accord with one embodiment of the present invention.
Figure 15B:
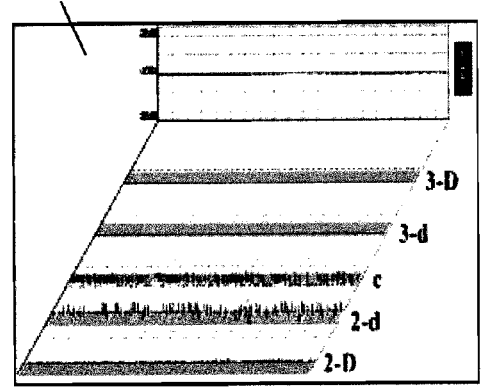
FIG. 15B shows an example of corrosion pitting in accord with one embodiment of the present invention.
Figure 15C:
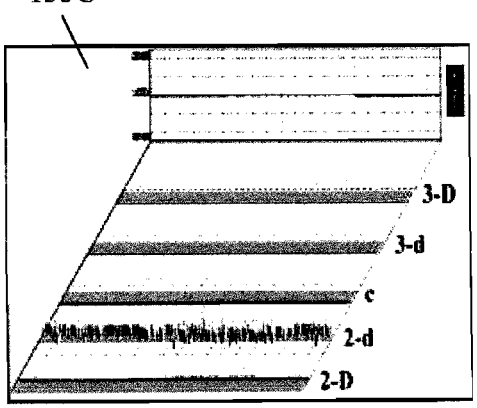
FIG. 15C shows another example of corrosion pitting but with features morphology migration as compared to FIG. 15B in accord with one embodiment of the present invention.
Figure 15D:
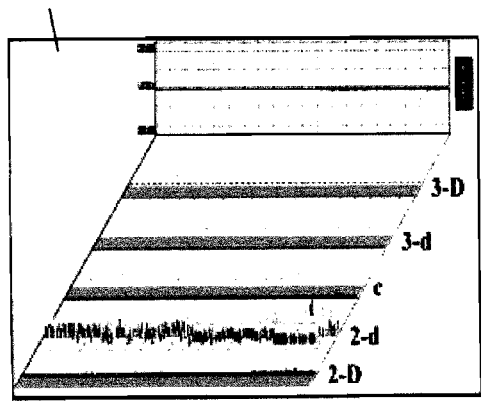
FIG. 15D shows an example of a shift towards fatigue cracking in accord with one possible embodiment of the present invention.
Figure 15E:
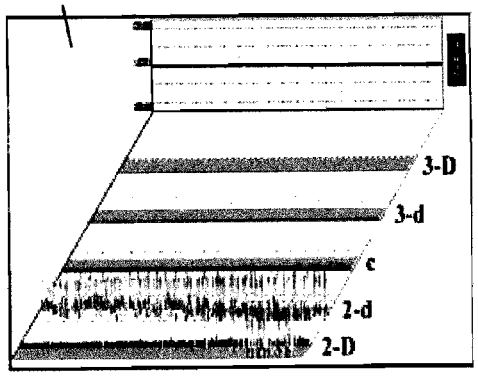
FIG. 15E shows an example of late fatigue life manifestation in accord with one possible embodiment of the present invention.

FIG. 14 illustrates an FFS flow chart in accord with one typical embodiment of the present invention. As mentioned earlier, AutoFFS assessment is based primarily on as-built or as-is data 110, 120 and 130. The first AutoFFS step is to separate design features and imperfections 140. When design data is available, AutoFFS also monitors compliance with the design data 142. Typically, once each imperfection has been identified, its severity 141A may be established by applying stress concentration correction factors and neighborhood information correction factors. The imperfection identification may also be utilized to establish the MUA 9 degradation mechanism 141B. An FFS for the feature is then calculated 141C.

For each feature, including imperfections, the acceptance/rejection criteria are then applied 142. When the degradation mechanism is known, preventive action 146 may reduce/prevent further MUA 9 deterioration, such as relocating the OCTG in a string, repairing damaged protective coating or using corrosion inhibitors. Conversely, comparison with previous FFS records 137 may measure the effectiveness of any prior preventive action. Occasionally, re-rating 148 the MUA 9 early on may result in an extended useful life in service 151.

When MUA 9 does not meet the minimum acceptable criteria for the application and it cannot be repaired 144, the MUA 9 may be re-rated and used in a different application 151. However, repeat AutoFFS scans should minimize the number of unanticipated MUA 9 rejections. MUA 9 deterioration should be tracked and preventive action 146 and 148 should maximize the MUA 9 useful life.

FIGS. 15A-15E illustrates FFS time sequence of a coiled tubing work coil in accord with one possible embodiment of the present invention. The baseline 155A shows the flaw spectrum of a new coil. Since CO2 is predominant in the work area, it is anticipated that future FFS scans would detect CO2 type corrosion (2-d). Preferably AutoFFS would include imperfection growth paths, morphology migration evaluation paths and root-cause identification. For example, the depth of a corrosion pit may increase and/or the corrosion pitting density may increase and/or a crack forming at the bottom of the pit would result in a critically flawed area (herein after referred to as "CFA"). CO2 type corrosion pitting appears in scan 155B exactly as expected and it is predominant by scan 155C. Scans 155B and 155C show features morphology migration. Because the work coil is undergoing bending in the plastic region (plastic deformation), the pits act as stress concentrators increasing the cyclic fatigue built-up rapidly. The morphology shift toward fatigue cracking (2-D) is shown in 155D along with significant growth. The work coil shown in 155D is no longer fit for service due to the imperfection severity (2-d). The only feasible remediation option is to remove the coil from service work and re-rate it 148 as a production string where the coil will no longer be subjected to plastic deformation cycles. However, since the coil is under continuous in-service monitoring, the coil was subjected to a few extra cycles, shown in 155E, when cracks (2-D) appeared, probably at the bottom of the CO2 corrosion pits (2-d). Cracks, a late fatigue life manifestation shown in 155E, grow rapidly and the coil would break within the next 3 cycles.

AutoFFS would preferably utilize a number of FFS paths, some dedicated into prognosis. For example, when computer 20 monitors, logs and evaluates the overall drilling performance, the FFS paths may be selected and its impact on the MUA 9. The impact of the drilling may be established by measuring the power consumption of the drilling process, the string weight, weight on bit, applied torque, penetration rate and other related parameters. Such information, an indication of the strata and the efficiency of the drilling process, may dictate that a different FFS path and/or constraints should be utilized to further evaluate the MUA 9 FFS including imperfections 140. Furthermore, changes in the strata and/or in the efficiency of the drilling process may indicate conditions that primarily induce imperfection morphology migration, not just growth, thus AutoFFS should also include the anticipated deterioration mechanism acting on the imperfections.

Feature Duration

As mentioned earlier, it should be understood that the one to one correspondence of simple imperfections to the STYLWAN Flaw Spectrum occasionally applies to machined (man-made) imperfections and not to the complex form imperfections typically found in nature. Therefore, the STYLWAN Flaw Spectrum elements must be viewed as an entity identification signature, just like DNA, but not as a detailed chemical analysis. It would be erroneous for example to conclude that a weld is made up form a pit, three gouges and a wall thickness increase, the result of a chemical-analysis-like interpretation of the Flaw Spectrum data. The correct Flaw Spectrum interpretation would recognize the signature of a weld and therefore, the first AutoFFS task would be to recognize complex imperfections, such as welds.

It should be readily apparent that complex imperfections would have significant 3D dimensions, as opposed to a single crack for example, and therefore their Flaw Spectrum would have a much longer time and/or length duration. If the AutoFFS was allowed to interpret signals instantaneously, the AutoFFS would behave erroneously, in a chemical-analysis-like fashion, where a weld would be reported as a string of pits, gouges, CFAS and wall thickness changes. For example, the feature shown in 155C is a corrosion band, not a large number of corrosion pits, and the root-cause of the corrosion band is identified as CO2. Therefore, preventive action 146 should focus at minimizing the impact of the CO2 environment on the work coil. Similarly, 155E shows multiple CFAs and borderline CFAs, not just pits and cracks. Therefore, interpreting 155C through 155E instantaneously may lead to erroneous conclusions and possible instability.

It is desirable therefore, that AutoFFS processing preferably incorporates feature duration data and/or trigger along with the ability to revisit prior data and/or decisions. It should be noted that any time delay between the feature passing through the head 2 and an AutoFFS decision would be insignificant and unnoticeable by the operator. Furthermore, it should be noted that feature duration refers to sufficient duration that would lead to a valid AutoFFS conclusion and not necessarily for the duration of the entire feature.

For example, a coiled tubing taper (a wall thickness change) may be many thousands of feet long while a localized wall loss could be six inches long. On the onset of such a feature, it would be advisable to examine a greater MUA 9 length, ten feet for example, before the AutoFFS makes a decision. At 180'/minute scanning speed, ten feet delay would amount to about one third ($\frac{1}{3}$) of a second that would certainly go unnoticeable by the operator. Furthermore, even the AutoFFS shortest utterance, like "taper" or "weld", would take longer than one third ($\frac{1}{3}$) of a second.

Complex Features

Again, complex features may be included in the MUA 9 by design, such as tapers, collars and welds, and therefore may be shown in the historical data records and/or may be anticipated; may reflect repairs and/or alterations that are not shown in the historical data records and may or may not be anticipated, such as a repair weld and lastly, they may reflect imperfections that were not encountered on previous AutoFFS scans. Once the complex features is recognized 140, AutoFFS processing would then proceed with the evaluation tasks prescribed for the particular complex features and its ramifications upon the AutoFFS processing.

As discussed earlier, AutoFFS may retain more than one identifier for redundancy, conflict resolution, and system stability. It should then be understood that the recognition of complex features may involve more than one identifier. Furthermore, complex features are the most likely cause of AutoFFS instability and as a precaution therefore, AutoFFS, once it reaches a decision, may re-examine the same features under longer duration. This re-examination diminishes the probability of instability and increases the AutoFFS certainty, especially if different identifiers are implemented for the re-examination.

Assessment of Welds

Welding is the joining of two material pieces by applying heat with or without the use of filler material. Rarely used cold welding is accomplished by applying high pressure. Welding induces residual stresses that FFS and FEA typically assume to be uniform throughout the material thickness (uniform stain field). During multipass welding for example, the same point undergoes multiple thermal cycles multiple times and secondly, not all points undergo the same number of thermal cycles. Therefore, it would be erroneous to assume that the weld residual stresses are uniform throughout the material thickness. The heat-affected zone (herein after referred to as "HAZ") is the portion of the base material that did not melt during welding, but the welding heat altered its properties.

Welds are complex features that are very common, just like couplings. Often, material with welds is derated, such as coiled tubing with a butt weld. In addition, a different derating factor is used for factory butt welds and field butt welds. AutoFFS cannot make that distinction automatically. However, AutoFFS may search the local or remote history and/or alteration record and/or may inquire for an entry from the operator 138 and/or an expert. In the absence of additional information, preferably AutoFFS would evaluate the weld as a complex feature, feature rating, and rate the material pessimistically, statutory rating. Preferably, AutoFFS would retain and report both ratings.

Fatigue Assessment

For centuries, practicing engineers recognized that subjecting metal to stress cycles resulted in fractures although the forces involved were a fraction of the forces required for static failure. The term Fatigue was introduced in the $19^{th}$ century probably by J. V. Poncelet (1788-1867). Fatigue initiates at the crystal imperfections, commonly known as dislocations. Dislocations can be viewed as atomic level microcracks that act as stress concentrators starting the slip mechanism. Fatigue is cumulative and with additional stress cycles, fatigue progresses to cracking as the microcracks grow and bridge, a point where failure is rapid.

Even the most sophisticated prediction models lack most of the detailed information required for a valid prediction. For example, OCTG may contain $10^{10}$ dislocations/in$^3$ on the average and while deployed may be subjected to unanticipated significant loads. Even if all the loads and the exact nature of each dislocation were precisely known, any type of calculation, such as FEA, would be prohibitive. Furthermore, the problem of fatigue cracks rapidly magnifies when the material is subjected to cyclic loading in corrosive environments.

The advantage of AutoFFS is the large number of repeated assessments and data that can be collected without interfering with the deployment of the MUA 9 or the production rate. AutoFFS detects the actual condition of the MUA 9 fatigue regardless of the underline causes. Fatigue build-up tests with the exemplary RDIS-10 revealed that fatigue up to ≈50% of the life cycle falls in the 2-Dα spectrum segment, between and ≈75% falls in the 2-Dβ spectrum segment and above ≈75% falls in the 2-Dγ spectrum segment.

Most software failure prediction models are aimed at predicting the alpha failure location (herein after referred to as "(αFL)"); the location where the rate of fatigue build-up is the highest and therefore, it is the location where the first failure is expected to occur. RDIS-10 fatigue build-up tests revealed that multiple (aFL) can be identified at the boundary transition between 2-Dα and 2-Dβ while the failure location can be identified at about 65% of the life cycle when preventive action 143 becomes extremely important.

The most catastrophic form of failure is Early alpha failure (herein after referred to as "(EαFL)") that is not predicted by any model but AutoFFS would easily detect 142 the rapid fatigue build-up. An (EaFL) most likely would be the result of MUI 1 that does not meet the specifications or material that was damaged during transportation and handling following the inspection.

Crack-Like Imperfection Assessment

In-service fatigue build-up typically initiates surface cracking. Cracks also initiate at the bottom of other imperfections, such as pits, that act as stress concentrator as shown in 155E. Modeling and predicting crack growth is extremely imprecise, just like modeling fatigue. Again, AutoFFS scans, preferably after every use, would track the actual crack growth and propagation regardless of the underline causes. A measure of the energy released per crack surface area may be calculated from the AutoFFS data. Without additional loads and when crack growth reaches its limit, AutoFFS may calculate the residual stresses that contributed to the crack growth. Such data may supplement the historical data of all materials deployed in similar applications. Preferably, such database would reside in a central remote location in communication with AutoFFS. Significant remaining useful life of the MUA 9 may be recovered if the crack 7A in FIG. 3A is morphed 145 into a 3-D type imperfection 7B (much lower stress concentration) as shown in FIG. 3B, but only if the neighborhood of crack 7A is free from other imperfections. Therefore, effective preventive action 146 is essential.

Crack growth and propagation is highly sensitive to changes in the application or the environment. As carried out, FFS assessment typically utilizes theoretical data and/or experimental data that were obtained in a laboratory under carefully controlled conditions. Such data are not always appropriate for field use. AutoFFS data on the other hand, reflect actual field conditions and material performance and therefore capture the actual material FFS for the particular application and/or environment.

Pitting Assessment

For isolated pits, 2-d through 3-d assessment would examine the proximity of other imperfections to the pit that may form a CFA under the regiment of anticipated loads as shown in 155E. Once the material is determined to be free of CFAs, discussed further below, AutoFFS would then establish severity of the pit.

For corrosion bands, 2-d through 3-d assessment would first establish the boundaries of the corrosion region (imperfection duration and area coverage). Then AutoFFS would determine if the corrosion region damage is still acceptable 142 and that the region is not growing at an unacceptable rate by utilizing previous FFS records 137, such as 155C and 155D. AutoFFS would then attempt to identify the nature of the corrosion mechanism. Different mechanisms result in different types of corrosion pitting such as narrow base cylindrical pits all the way to broad based conical pits and FDDim may be used as a corrosion mechanism guide and thus a guide to the root-cause identification and the proper remediation 145, 146.

For example, when $CO_2$ type pits appear on MUI 1 that was free of $CO_2$ pits in previous AutoFFS scans, it is reasonable to conclude that $CO_2$ backflooding has reached the particular well site. This change in the operating environment significantly impacts the remaining MUA 9 life which can be recalculated and extended by the proper application of inhibitors or by simply rearranging the tubing in a well. Furthermore, early detection of the $CO_2$ presence may redefine the next preventive maintenance service interval. This unique and novel feature of the AutoFFS is not available with the sporadic inspections which more likely would take place after the MUA 9 failed prematurely because of the accelerated $CO_2$ corrosion.

This example also demonstrates another AutoFFS strength versus FFS and 1D-NDI as carried out. Lets assume that the production tubing was in a well for 4 years prior to $CO_2$ reaching the well site and that a tubing failure occurs 1 year after $CO_2$ reached the well site. FFS assessment and 1D-NDI would then reasonably conclude that the tubing time to failure in the particular well is 5 years (tube useful life), when in fact it is only 1 year. Due to costs involved, it is unlikely that 1D-NDI would be deployed during a workover and even if 1D-NDI is deployed, 1D-NDI could not detect the change in the environment. By the time the owner figures out the new oilfield realities, following multiple tubing failures, a vast number of production tubing strings may need replacing while an AutoFFS assessment would alert the owner about the subterranean environment changes and recommend a preventive action 143 early on, thus extending the life of multiple production strings. It should then be understood that AutoFFS frequent utilization, preferably on every workover, could have significant ramifications for the entire operation, not just the particular well.

Critically Flawed Area Assessment

CFA is a complex encounter where imperfections in proximity are dynamically linked under loading, such as a corrosion pit with a crack at the bottom (similar to the CFA of FIG. 3C) or imperfections in proximity and orientation as to experience increased stress concentration. The detection of such a CFA early on may not necessarily mean rejection of MUA 9 as simple precautions 146, such as minimizing the cycling of the particular MUA 9 location, may be sufficient and it may extend the use of the MUA 9. In addition, with a AutoFFS continuously monitoring the CFA, the full useful life of the MUA 9 may be used despite the presents of the CFA as long as the CFA growth and/or morphology migration remain within acceptable limits as shown in 155D and 155E.

It should also be noted that the AutoFFS processing is diametrically opposing the 1D-NDI processing whereby a single uncorrected signal is used to pass or send the material for verification. Since the uncorrected signal of a small crack at the bottom of a pit does not significantly alter the pit signal, 1D-NDI would pass the material with the CFA as long as the pit signal itself does exceed the preset magnitude limit. It is also important to observe that corrosion pits occur at the surface of materials and in materials that endure dynamic loading, such as coiled tubing, drill pipe and marine drilling risers, the pits, the welds and other imperfections act as stress concentrators. Cracking would then initiate at the stress concentrators, like the bottom of the pits or the heat affected zone of welds, but such CFAs would go unnoticed by the TOFD of U.S. Pat. No. 6,904,818 because the CFAs would fall within the TOFD near-surface and far-surface detection dead-zones.

3-d and 3-D Assessment

Imperfections like grooves and gauges along with material hardness changes typically fall into this segment of the flaw spectrum. Grooves typically arise from erosion or corrosion while gauges are mostly the result of mechanical damage. Dents and deformations, discussed further below, often include gauges, scratches and notches. 2-D and 2-d remediation action, as shown in FIG. 3B, also results in imperfections that typically fall into this segment.

When an excavator accidentally hits a pipeline, it will dent it, thus it would plastically change the pipeline material. Interaction with the environment may change the material properties and it may change the plastically deformed dent region at a different rate than the undamaged pipeline material. During pumping, the pipeline pressure varies at a frequency that may lead to a crack in the deformed area.

Hardness estimates the strength of the material and its resistance to wear. Hardness changes, such as a hard spot, effect the remaining useful life of the MUA 9 differently from wall thickness related features. For example, in material enduring cycles of tension and compression the vicinity of the hard spot would experience significantly increased loading and increased fatigue built-up, a potential (EaFL).

Wall Thickness Assessment

Wall thickness assessment may utilize the wall thickness profile (minimum, nominal, design, maximum), the wall thickness variation profile, the cross-sectional area profile and the average wall thickness profile, preferably all covering one-hundred percent (100%) of the MUI 1 continuously.

As mentioned earlier, wall thickness changes, by design or otherwise, may be used to alter the AutoFFS processing. For example, a pipe coupling would appear as a significant wall thickness increase and may be used to invoke the AutoFFS coupling inspection.

3-G Deformation Assessment

Irregularities in the MUA 9 geometry, such as balooning, dents, eccentricity, neck-down, ovality, misaligned welds and straightness typically fall into this category. Deformations may originate in manufacturing, such as eccentricity; may be the result of a repair, such as a misaligned weld and lastly deformations may be induced during deployment, such as dents, ovality and balooning. Dents and gouges are typically the results of mechanical action, such as an excavator hitting a pipeline. The fact that material is not straight, such as a bend drill pipe joint, is an indication that the material's yield strength was exceeded during deployment. A bend drill pipe joint would most like vibrate, increase the fatigue build-up and increase the wear on both the joint and any casing is deployed through.

Coiled tubing endures plastic deformation and it is an example of use induced deformation. When tubing bends, the fibers at the major axis have to travel further (extend) than the fibers on the minor axis (compress). This involves an amount of stored energy. In order to minimize the amount of stored energy, the tube swells sideways (neutral axis) and assumes an oval cross-section (ovality). By doing so, it minimizes the major axis fiber extension and the minor axis fiber compression. AutoFFS uses 3-G information directly and/or as a processing selection guide.

Material Deployment Loads

During deployment, materials may experience bending, buckling, compression, cyclic loading, deflection, deformation, dynamic linking, dynamic loading, elastic deformation, eccentric loading, feature propagation, impulse, loading, misalignment, moments, offset, oscillation, plastic deformation, propagation, shear, static loading, strain, stress, tension, thermal loading, torsion, twisting, vibration, and/or a combination thereof.

As it is well known, MUA 9 features behave differently under different loading and therefore AutoFFS would have to evaluate the features it encounters under all the anticipated types of loading 140 and any combination thereof. For example, drill pipe in a dog leg would also be subjected to bending in addition to torsion and loading. Furthermore, re-rating 148 MUA 9 early on may extend the MUA 9 useful life.

AutoFFS Feasibility

The overall system must be feasible not only from the classification standpoint but also from the realization standpoint. In addition to the classification and minimum error, the system constrains also include, but are not limited to, cost, packaging, portability, reliability, and ease of use; all of which should be addressed in each step of the design. The system design preferably must assign initial resources to each level and should attempt to minimize or even eliminate resources whose overall contribution is negligible. This can be accomplished by converting certain features to bias and evaluating the resulting error.

Computer 20 preferably recognizes the feature by comparing the final array of identifiers 135, 136, 139 with a stored features template database. Once a feature is recognized, computer 20 may verify the correctness of the recognition by further evaluating intermediate identifiers.

AutoFFS Instability and Conflict Resolution

Occasionally, the feature recognition becomes unstable with the final array of identifiers toggling between two solutions on each iteration. For example, during the inspection of used production tubing, the recognition may bounce back and forth between a large crack or a small pit. Resolution of such instability may be achieved by varying the feature duration length, utilizing intermediate identifiers, by utilizing the previous recognition value, or by always accepting the worst conclusion (typically referred to as pessimistic classification). However, AutoFFS instability may also be the outcome of improper backwards chaining or even faulty constrains. Slight increase in the coefficients of the backwards chained features may produce an output oscillation thus rapidly locating the problem feature and/or coefficients.

A conflict arises when the final array of identifiers points into two or more different MUA 9 conditions with equal probability. Again, resolution of such conflict may be achieved by utilizing intermediate identifiers, by utilizing the previous recognition value or by always accepting the worst conclusion. However, a definite solution may be obtained by eliminating features that the conclusions have invalidated and by reprocessing the signals under the new rules.

The AutoFFS is preferably designed to reason under certainty. However, it should also be capable of reasoning under uncertainty. For example, during the assessment of used production tubing of a gas well, rodwear is detected. Since there are no sucker rods in the gas well, the conclusion is that this is either used tubing that was previously utilized in a well with sucker rod or there is a failure in the AutoFFS. The AutoFFS could query the operator 138 about the history of the tubing and specifically if it was new or used when initially installed in the well. The answer may be difficult to obtain, therefore a 50-50 chance should be accepted. A bias value may then be altered and the signal may be reprocessed under the new rules.

Alternate coefficients may be stored for use when certain failures are detected. For example, the wellhead pressure transmitter may fail. Upon detection of the failure, the alternate set of coefficients should be loaded for further use. It should be understood that even a simple bias may substitute for the failed transmitter.

FFS Calibration Sample

FIG. 16A illustrates a calibration sample with four features for use with AutoFFS to evaluate the AutoFFS feature identification capabilities and tune its parameters for the specific FFS needs of the particular material/application. Imperfection 156A is a crack-like imperfection, 156B is a pit-like imperfection, 156C is a gouge-like imperfection and 156D is a wall thickness feature. It should be understood that the calibration sample may contain multiple features and/or multiple examples of similar features with varying geometries. It should further be understood that features may be located on the OD or the ID of the material or both the OD and ID.

FIG. 16B illustrates a calibration sample with two coexisting imperfections for use with AutoFFS to evaluate the AutoFFS coexisting imperfection separation and identification capabilities and tune its parameters for the specific FFS needs of the particular material/application. Imperfection 157 is a crack-like imperfection coexisting with a pit-like imperfection. It should be understood that the calibration sample may contain multiple coexisting features and/or multiple examples of similar coexisting features with varying geometries. It should further be understood that coexisting features may be located on the OD or the ID of the material or both the OD and ID.

Not shown are calibration samples with additional features, such as couplings, welds, deformation and the like, that may be utilized, as dictated by the particular material and/or application. Therefore it would be appreciated that standard threaded connections and/or welded sections, and the like, may be used for calibration.

FIG. 16C illustrates a range of 1D-NDI recommended calibration/reference imperfections. It is of interest to notice the machining precision specified for the reference imperfections. As a general rule, the tighter the machining tolerances for the reference imperfection, the least likely the imperfection would be encountered in nature. Furthermore, MUI with any diameter pit, 1/16" or otherwise, should be rejected for further use way before the pit becomes a hole (100% penetration), regardless of the machining tolerances. Again, as shown in FIGS. 2A and 2B, 1D-NDI would easily mislead someone to believe that a 5% notch or a 100% pit (a hole) are appropriate calibration/reference standards and the tight machining tolerances add a false sense of confidence in 1D-NDI.

FIG. 16D illustrates yet another situation that 1D-NDI would mislead the inspector. Imperfection 159 consists of a number of imperfections 158. The highest signal selector 10 of 1D-NDI would propagate to the readout 5 the signal of only one of the imperfections 159 resulting in an identical inspection trace for imperfections 158 and 159. Strength of material knowledge (and common sense) teaches that the MUA 9 will break at 159 when subjected to loads such as bending, torsion, cyclic loading etc. If imperfection 158 did not cross the 1D-NDI threshold level, then 159 will not cross the 1D-NDI threshold level either due to the 1D-NDI signal processing. Even if imperfections 158 and 159 did cross the 1D-NDI threshold level, it is unlikely that 159 would be recognized as a CFA by the verification crew and it is highly unlikely if imperfections 158 and 159 were located in the ID of MUA 9. On the other hand, AutoFFS would evaluate each 159 imperfection on its own and apply neighborhood correction factors, thus distinguishing imperfection 159 from 158.

Remediation

As discussed earlier and referring back to FIG. 3, 1D-NDI will typically miss imperfection 7B as it will also miss FIG. 16D imperfection 159. Furthermore, 1D-NDI recommended remediation for imperfection 7A does not account for the vicinity of imperfection 7A. For example, if imperfection 7B was located on the ID below imperfection 7A, the 1D-NDI remediation action for 7A would instead result in a differently defective material that is acceptable by 1D-NDI but rejectable by AutoFFS.

AutoFFs must calculate the optimal remediation profile along with the remediation feasibility. For example, it will be straight forward for AutoFFS to calculate the optimal remediation profile 7B for external imperfections 7A or 158 and such remediation is feasible. It will be by far more complex to calculate the optimal remediation profile for external imperfections 159. AutoFFS will first calculate the optimal remediation profile for each one of the imperfections making up 159. AutoFFS would then examine the neighborhood for each morphology shifted imperfection making up 159. This may result in a remediation profile that is no longer optimal and therefore, AutoFFS will calculate an optimal remediation profile combining two or more of the morphology shifted imperfections making up 159. This iterative process may continue until an optimal remediation profile for 159 is calculated or until AutoFFS decides that no remediation is feasible. For example, repeat remediation iterations for imperfection 159 may lead to an optimal remediation profile resulting in a groove around the circumference of MUA 9. This groove may render MUA 9 unfit for continuing service. AutoFFS would then have to calculate an optimal remediation profile for the groove that would result in a fit for continuing service MUI or re-rated 148 MUI. Therefore, AutoFFS optimal remediation profile calculations will continue until at least two consecutive unfit for service calculations have been performed.

NDI and AutoFFS Utilization

Figure 17:
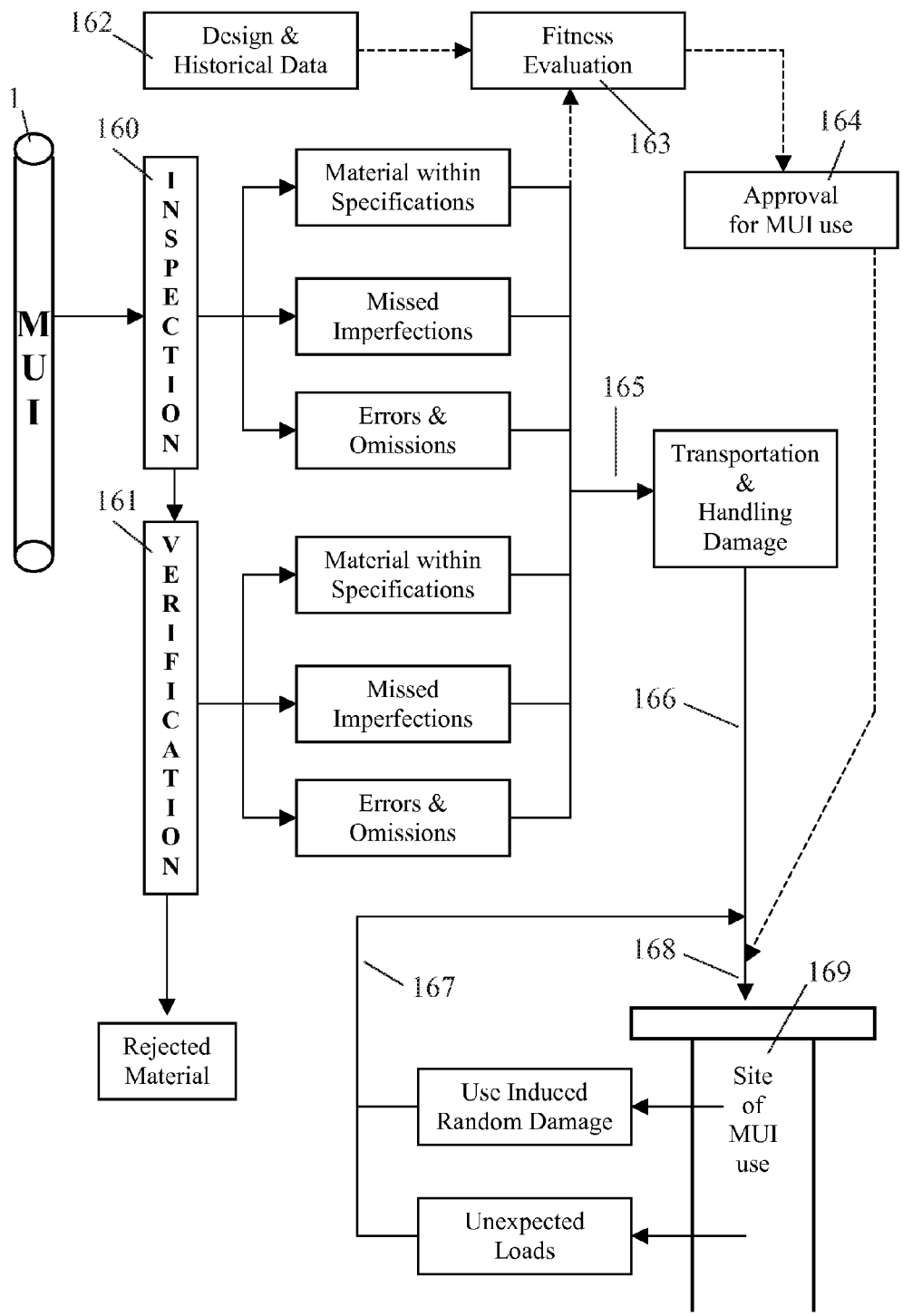
FIG. 17 illustrates a block diagram of an NDI process in accord with one possible embodiment of the present invention.

FIG. 17 illustrates an NDI process in accord with one possible embodiment of the present invention. As practiced today, NDI dictates termination of the material utilization altogether in order to accommodate the inspection process, which, is typically carried out by shipping the material to an inspection facility. The cost of inspection is therefore increased by the transportation cost and the material downtime. In addition, shipping and handling the material, especially after the inspection 165, may induce damage to the material that could result in an unanticipated early catastrophic failure.

During inspection 160, the MUI 1 is examined for indications (flags), such as "regions of abnormal magnetic reluctance (or echo, or phase shift etc)", that exceed a preset threshold level. A typical 1D-NDI equipment "standardization" practice sets the threshold level by scanning a "reference standard" as shown in FIG. 16G. Again, referring back to FIGS. 2A and 2B, it is easy to see how someone may be mislead to believe that "standardization of the 1D-NDI equipment" would somehow be equally accomplished by "referencing" a 1D-NDI unit on a "through-wall drilled hole", a 3-d imperfection with 0% remaining wall thickness, or a "5% OD notch", a 2-D imperfection with 95% remaining wall thickness. Therefore, the 1D-NDI equipment is "standardized" to flag imperfections with wall loss anywhere between 5% up to 100% depending on the geometry of the imperfection; the 1D-NDI practice that led to the material failure illustrated in FIGS. 2A through 2D. The flagged material is then send for verification 161.

Material 165 may then contain an assortment of imperfections, some because of the 1D-NDI "standardization" practice, like an 75% drilled hole; some because of missed imperfections, due to "sensor liftoff" or "detection dead-zones", and some because of errors and/or omissions either by the inspector or by the verification crew. Material 165 is then exposed to potential accidental damage during transportation and handling to the site of use 169. During deployment, the material may endure unexpected loads or suffer unexpected damage 167, but the condition of the material 168 will not be ascertained again until the next inspection cycle or after a failure.

Because of its implementation and the intrusion NDI imposes, typical inspections have been expensive and are thus performed at rare intervals or not performed at all. For example, NDI costs of OCTG can be as high as 30% of the material replacement cost.

In the rare occasion that an analysis follows the NDI, the inspection results 163 are send for evaluation while the material is shipped to the use site 169. The evaluation process 164 may incorporate design and historical data 162 and eventual approval for the material use may be granted well after the material has reached the use site 169. Because of the evaluation process 163 inherent delay and cost, along with other economic pressures, the material 166 is typically put to use immediately upon arrival at the use site 169 and the evaluation process is reduced to a search for the failure mechanism of the rejected material.

Pipelines on the other hand, are typically inspected by internal inspection units commonly known as pipeline pigs or pigs. Following the scan, the inspection data is sent for evaluation 163 while the pipeline is put back into service. It is obvious that areas of concern cannot be identified until trained inspectors examine the inspection data, a process that typically takes weeks if not months. It is not uncommon for a verification report to be generated months after the inspection identifying hundreds of areas of concern requiring manual verification. Manual verification for pipelines involves crews with heavy equipment that would travel to the designated areas, dig up the pipeline and perform manual inspections to evaluate the nature and extent of the imperfections that gave rise to the pig signals. The verification results would then be sent for evaluation 163 and approval 164, months after the pipeline was put back into service following the inspection. In the meanwhile, a pipeline leak may develop in one of the areas designated for verification or even in an area that was not flagged by the pig. Such detection failure may arise from the 1D-NDI limitations that result in specialized inspection pigs such a pitting inspection pigs, crack inspection pigs etc.

On the other hand, AutoFFS must examine and evaluate, as close as possible, 100% of the MUA 9 for 100% of pertinent features and declare the MUA 9 fit for continuing service only after the impact of all the detected features upon the MUA 9 have been evaluated; diametrically opposing the 1D-NDI methodology. It is well known that the presence of any imperfection alters the expected (designed) life of the MUA 9 and thus impacts its remaining useful life. Thus, it should be appreciated that the deployment of the AutoFFS would increase the overall safety and reliability as it would lead to MUA 9 repair/replacement prior to a catastrophic failure as well as it will reduce and/or eliminate its premature replacement due to concerns when the conventional inspection periods are spaced far apart and/or when the conventional inspection provides an insignificant inspection coverage.

Figure 18:
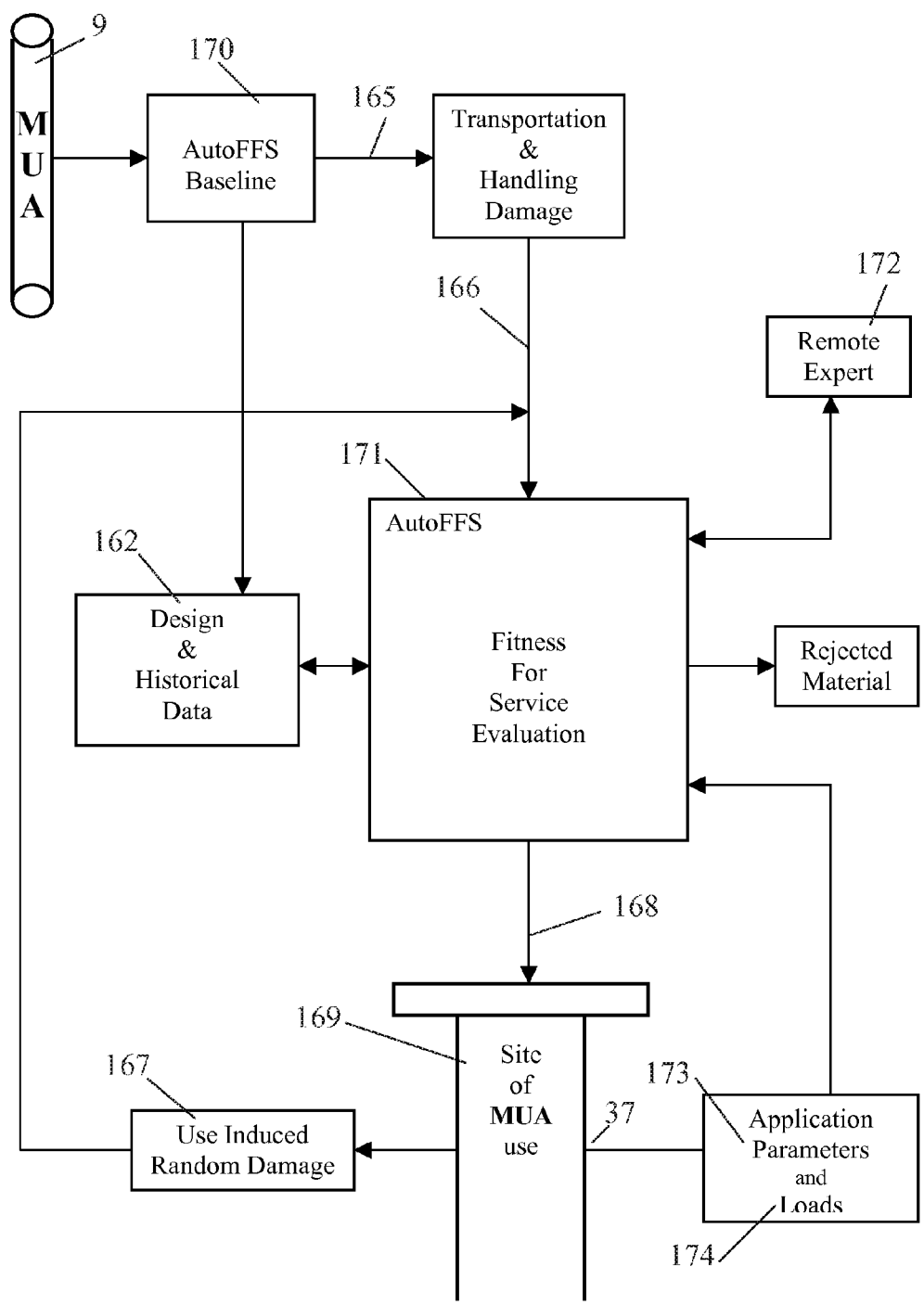
FIG. 18 illustrates a block diagram of the AutoFFS process according to the present invention.

FIG. 18 illustrates a typical AutoFFS process. Preferably, an AutoFFS baseline 170 is obtained prior to the deployment of the MUA 9. It should be understood that any subsequent onsite AutoFFS scans 171 become the baseline, historical data 162, for the next scan, therefore, the first baseline may also be obtained during the first AutoFFS scan 171 at the deployment site 169. Onsite AutoFFS scans 171 would assure that material 168 is still fit for service "as-is" including any transportation and/or handling damage 166 or any use-induced damage 167. A remote expert 172 may review the AutoFFS data, may convert and run the AutoFFS data with finite element analysis engine and/or may alter the AutoFFS processing.

FIG. 9 illustrates an AutoFFS operator readout 180 configured for drill pipe in accord with a typical embodiment of the present invention. It should be understood that the AutoFFS operator readout 180 is provided in addition to the speech and sound interface. It should be further understood that this particular AutoFFS implementation is for illustration purposes only and should not be interpreted as limiting in any fashion. This particular AutoFFS operator readout 180 comprises of the NDI readout 181, the AutoNDI readout 182 and the AutoFFS readout 183. This particular AutoFFS assigns a fitness number to the MUA 9 between 0 and 100. Fit for service material is assigned a number between 50 and 100 (green). Material that is fit for service under continuous monitoring is assigned a number between 25 and 49 (yellow). Unfit for service material is assigned a number between 0 and 24 (red).

The NDI readout 181 shows a drill pipe joint body wall, a tool joint 184 (a complex feature) and a second joint with a machined wall loss 185. As discussed earlier, if the AutoFFS was allowed to interpret the tool joint 184 signals instantaneously, the AutoFFS would behave erroneously, in a chemical-analysis-like fashion, and will report that the tool joint is made up of wall thickness increase and a number of assorted imperfections. Instead, AutoFFS feature duration processing identified the tool joint 186, altered the processing path and calculated the FFS of the tool joint 188 using a different assessment path than the drill pipe body wall path 187. This particular AutoFFS assessment declared both the drill pipe body wall 187 and the tool joint 188 fit for service (green—above mid point). AutoFSS assessed a short section of the machined wall loss 189 as fit for service under continuous monitoring (yellow—below mid point) and the rest of the machined wall loss 190 as unfit for service (red). All of the AutoFFS data are available for examination by the operator and the remote expert 172. Similarly, the internal memory of an AutoFFS pipeline pig can be examined rapidly in minutes instead of weeks or months. The pipeline can be put back to service with confidence or the remediation effort can start immediately with the areas that were determined to be unfit for service. In addition, FEA can also be utilized to augment and/or verify the AutoFFS data as an additional safety measure.

Exporting AutoFFS Data to an FEA Engine

With the advent of desktop computers and design/drafting software, FEA is in wide use today. It is typically utilized during the design phase to analyze as-designed structures. It should be understood that FEA engines operate on physical structures (something) under static or dynamic loading, not features alone, as features alone do not exist in nature. For example, a corrosion pit does not exist on its own. A corrosion pit exists as a feature on a physical structure, such a pipeline. Typically, the geometry of a feature is expressed as percentage of the physical structure geometry. For example, a 10% pit depth is a meaningless expression without knowing the wall thickness of the material, the physical structure. Therefore, a 10% pit on a 0.095" wall thickness coiled tubing has a depth of 0.0095" and on a 1.000" wall thickness riser auxiliary line has a depth of 0.100". AutoFFS (and NDI), typically relay to the operator information regarding the severity (presence) of a feature (imperfection, defect) in a format such as shown in FIG. 2A, FIG. 2C and FIG. 19.

Figure 3D:
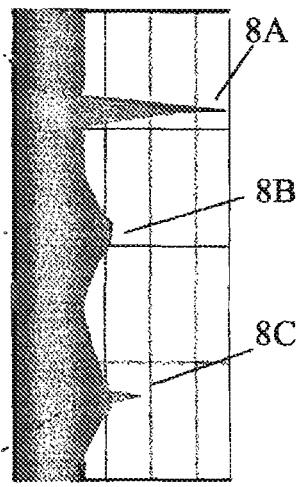
FIG. 3D illustrates the stress concentration.
Figure 19:
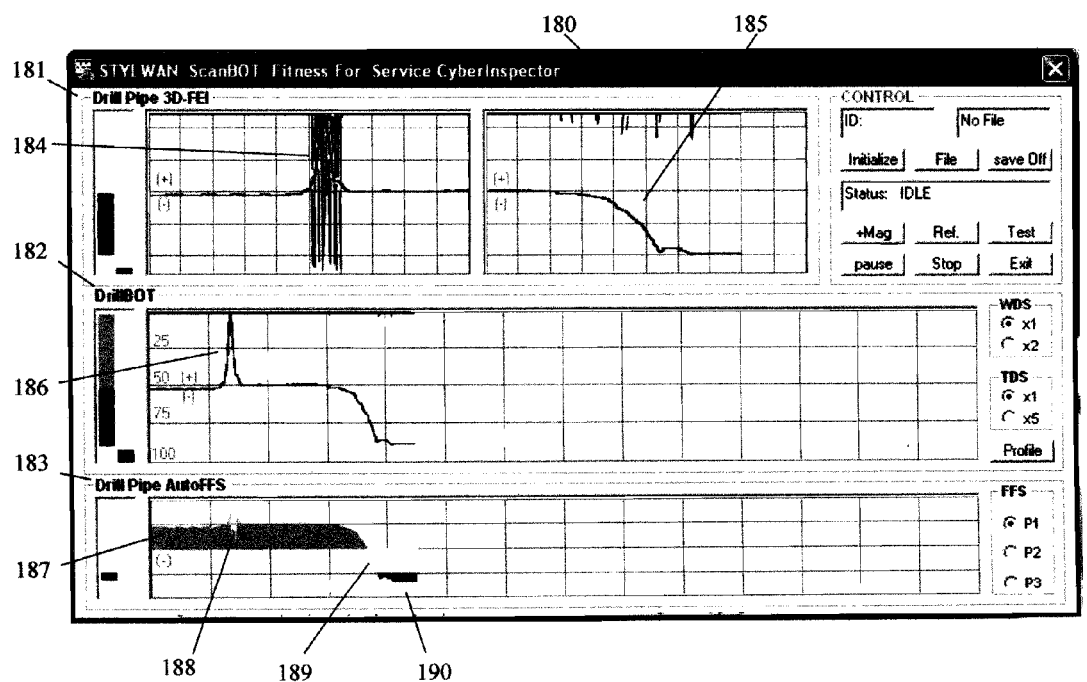
FIG. 19 illustrates an AutoFFS computer readout.

However, FEA Engines cannot operate on data, such as shown in FIG. 2C and FIG. 19. FEA Engines can only operate on a structure, such as shown in FIG. 3A through FIG. 3C, and evaluate the localized stresses of the structure under specific loading, as shown in FIG. 3D. It should be noted that 1D-NDI data are insufficient for FEA as 1D-NDI processing eliminates most of the material features information, as discussed earlier.

On occasion, it is desirable to analyze the as-is material with FEA to obtain, for example, deflection, strains, stresses, natural frequencies and similar data. Converting manually the AutoFFS signals to a structure requires a number of multi-discipline experts and it is time consuming. Therefore, it is desirable to provide a program that can convert automatically the AutoFFS material features to a geometrical structure for use by a commercially available FEA engine. It should be understood that such conversion would depend on the particular AutoFFS capabilities and the particular FEA engine geometry file specifications. A more general AutoFFS conversion would translate the AutoFFS data to a drawing for use by a commercially available drafting program, such as AutoCAD. Other commercially available programs would then export the drawing data to an FEA engine.

Having a physical description of the MUA 9 (structure) alone is insufficient information for FEA, as the loads involved are also required. Typically, the MUA 9 is analyzed under a regiment of anticipated loads that reflect the opinion of experts. A unique feature of AutoFFS is the data acquisition system 35 and sensors 36 and 37. As discussed earlier, computer 20 may also monitor, through the data acquisition system 35, parameters that are related to the assessment or utilization of the MUA 9 and/or parameters to facilitate FFS and/or remaining useful life estimation. Such parameters may include, but not be limited to, the MUA 9 pump pressure, external pressure, such as the wellhead pressure, temperature, flow rate, tension, weight, load distribution, fluid volume and pump rate and the like. Preferably, these parameters are measured or acquired through sensors and/or transducers mounted throughout the MUA 9 deployment area 169, such as a rig or on the MUA 9, such as a vibration monitor. For ease of understanding, these various sensors and transducers are designated with the numeral 37. Therefore, and in addition to the physical description of the MUA 9, AutoFFS would also acquire and export information regarding the actual deployment condition parameters 173 and the actual loads 174, including actual and the unanticipated loads the MUA 9 endures resulting in a as-is and as-used FEA.

It should be understood that not all AutoFFS features can be converted to a geometrical structure for use by an FEA engine, such as fatigue. Instead, such features affect the remaining useful life of the material. It should be further understood that setting the FEA boundaries and accepting, interpreting and understanding the overall FEA process data and results is beyond the anticipate capabilities of the onsite AutoFFS operator, and therefore, this task is assigned to a remote expert 172 or group of experts.

It may be seen from the preceding description that a novel Autonomous fitness for continuing service assessment system and control has been provided that is simple and straightforward to implement. Although specific examples may have been described and disclosed, the invention of the instant application is considered to comprise and is intended to comprise any equivalent structure and may be constructed in many different ways to function and operate in the general manner as explained hereinbefore. Accordingly, it is noted that the embodiments described herein in detail for exemplary purposes are of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A method to evaluate material comprising:
   inducing excitation into said material;
   detecting an output of at least one sensor, said output comprising of signals indicative of features from the material under evaluation, in a time-varying electrical form;
   decomposing in frequency said signals, wherein said decomposing comprises passing said signals through at least one filter, producing decomposed in frequency signals;
   converting said decomposed in frequency signals to a digital format producing digital signals;
   recognizing a feature by utilizing a computer to analyze said digital signals;
   evaluating an impact of said material feature upon said material under evaluation, utilizing said computer; and
   calculating a fitness for service of said material under evaluation, utilizing said computer.

2. The method of claim 1, further comprising the step of decomposing in frequency said signals, wherein said decomposing comprises passing said signals through a filter bank.

3. The method of claim 1, wherein said excitation is an electromagnetic excitation.

4. A method to calculate a material remediation comprising:
   programming a computer to operate a material features acquisition system to detect a plurality of material features in a material;
   recognizing a material feature utilizing said computer;
   evaluating an impact of said material feature upon said material, said evaluation being performed by said computer;
   calculating a fitness for service of said material, said calculation being performed by said computer; and determining a material remediation path, said determination being performed by said computer.

5. The method of claim 4, wherein said material remediation path comprises at least one of utilization, redeployment and alteration to a shape of said material feature.

6. The method of claim 5, wherein said step of determining a material remediation path comprises an said alteration to a shape of said material, said alteration to said shape being feature is an optimal shape for a redetermined fitness for service.

7. The method of claim 6, wherein said material remediation path comprises additional monitoring sensors for monitoring how said material is utilized.

8. A method to evaluate material comprising:
 detecting an output of at least one sensor, said output comprising of signals indicative of features from the material under evaluation, in a time-varying electrical form;
 converting said signals to a digital format producing digital signals;
 recognizing a material feature by utilizing a computer to analyze said digital signals;
 calculating a geometry of said material feature of said material under evaluation with said material feature, utilizing said computer; and
 converting said geometry to a file format in compliance with a finite element analysis engine input/output file specification.

9. The method of claim 8, further comprising the step of inducing excitation into said material.

10. A method to evaluate material comprising:
 inducing excitation into said material and detecting material features in said material with a material features acquisition system whereby digital signals are produced representative of as-is material features; and
 converting said digital signals into a data format for use by a finite element analysis program.

11. The method of claim 10 further comprising producing a finite element analysis of at least a portion of said material utilizing said finite element analysis program.

12. The method of claim 11 wherein said finite element analysis comprises evaluating stresses on said at least of portion of said material on a basis comprising specific loading.

13. The method of claim 12 wherein said specific loading comprises anticipated loads.

14. The method of claim 12 wherein said specific loading comprises measured loads.

15. The method of claim 12 wherein said specific loading comprises at least one of deflection, strains, stresses, natural frequencies, pump pressure, external pressure, wellhead pressure, temperature, flow rate, tension, weight, load distribution, fluid volume, vibration, and pump rate.

16. The method of claim 10 wherein said step of detecting material features comprises detecting an output of at least one sensor, said output comprising signals indicative of said material features from said material in a time-varying electrical form.

17. A system to evaluate a material comprising:
 a material features acquisition system operable to induce excitation into said material to detect material features of said material and produce data representative of said material features; and
 at least one computer programmed to convert said data into a data format for use by a finite element analysis program.

18. The system of claim 17, further comprising said at least one computer being programmed with a finite element analysis program to be operable to produce a finite element analysis of at least a portion of said material.

19. The system of claim 18 wherein said finite element analysis is programmed to evaluate stresses on said at least said portion of said material wherein said evaluation comprises specific loading input into said finite element analysis program.

20. The system of claim 19 wherein said specific loading comprises anticipated loads.

21. The system of claim 19 further comprising one or more loading sensors wherein said specific loading comprises measured loads.

22. The method of claim 19 wherein said specific loading comprises at least one of deflection, strains, stresses, natural frequencies, pump pressure, external pressure, wellhead pressure, temperature, flow rate, tension, weight, load distribution, fluid volume, vibration, and pump rate.

23. The system of claim 19 wherein said material features acquisition program comprises at least one sensor which produces an output comprising signals indicative of said material features from said material in a time-varying electrical form.

24. A material evaluation system comprising:
 at least one computer;
 at least one finite element analysis program;
 a material features acquisition system operable to detect at least one material feature in said material under evaluation;
 at least one database comprising at least one of material features recognition equations and material historical data;
 at least one program being executed on said at least one computer to recognize said at least one material feature and to convert said at least one material feature into a data format for use by said finite element analysis program;
 whereby said finite element analysis program being executed on said at least one computer is operable to produce a finite element analysis of at least a part of said material.

25. The material evaluation system of claim 24, wherein said at least one database further comprises at least one of equations, knowledge, rules and coefficients for at least one of bending, buckling, compression, cyclic loading, deflection, deformation, dynamic linking, dynamic loading, eccentricity, eccentric loading, elastic deformation, energy absorption, feature growth, feature morphology migration, feature propagation, impulse, loading, misalignment, moments, offset, oscillation, plastic deformation, propagation, shear, static loading, strain, stress, tension, thermal loading, torsion, twisting, vibration, similar items and combinations thereof, said at least one of equations, knowledge, rules and coefficients being used by said finite element analysis program to produce said finite element analysis of at least a part of said material.

26. The material evaluation system of claim 24, wherein said material features acquisition system is operable to induce an excitation into said material under evaluation wherein said induction of excitation is controlled, at least in part, by said at least one computer.

27. The material evaluation system of claim 24, whereby a boundary for said finite element analysis program is obtained at least in part from at least one of a speech recognition engine, a sound recognition engine and a camera.

28. The material evaluation system of claim 24, wherein said at least one database comprises captured knowledge of at least one expert in finite element analysis.

29. A material evaluation system comprising:
- at least one computer;
- a material features acquisition system operable to detect a plurality of material features in a material under evaluation; and
- at least one program being executed on said at least one computer to recognize said plurality of material features and to convert said plurality of material features into a data format for use by a finite element analysis program.

30. The material evaluation system of claim 29, wherein said at least one program further comprises said finite element analysis program.

31. The method of claim 30 wherein said finite element analysis is programmed to evaluate stresses on said material wherein said evaluation comprises specific loading input into said finite element analysis program.

32. The method of claim 31 wherein said specific loading comprises anticipated loads.

33. The method of claim 31 further comprising one or more loading sensors wherein said specific loading comprises measured loads.

34. The method of claim 31 wherein said specific loading comprises at least one of deflection, strains, stresses, natural frequencies, pump pressure, external pressure, wellhead pressure, temperature, flow rate, tension, weight, load distribution, fluid volume, vibration, and pump rate.

35. The material evaluation system of claim 29 wherein said conversion of recognized plurality of material features into said data format for use by said finite element analysis program converts said recognized plurality of material features into an as-is material operational model.

36. The material features evaluation system of claim 29, further comprising at least one database comprising at least one of material features recognition equations and material historical data.

37. A material evaluation system comprising:
- at least one computer;
- at least one finite element analysis program;
- a material features acquisition system operable to detect at least one material feature in said material under evaluation for detection of as-is material;
- at least one database comprising at least one of material features recognition equations and material historical data;
- at least one program being executed on said at least one computer to recognize said at least one material feature and to convert said at least one material feature into an as-is material operational model for analysis by said at least one finite element analysis program.

38. The material evaluation system of claim 37 whereby said as-is material operational model is operated by said at least one computer, said operation being guided by said at least one database to make a determination of an operational range of said as-is material.

39. The material evaluation system of claim 37 wherein said material historical data further comprise at least one as-designed material operational model whereby said at least one computer may compare said operational range of said as-is material with an operational range of an as-designed material.

40. The material evaluation system of claim 37 wherein said material historical data further comprise at least one prior as-is material operational model of prior as-is material whereby said at least one computer may compare said operational range of said as-is material with an operational range of said prior as-is material.

41. A method to evaluate material comprising:
- detecting an output of at least one sensor, said output comprising of signals indicative of features from the material under evaluation, in a time-varying electrical form;
- recognizing a material feature by utilizing at least one computer; and calculating a geometry of said material feature utilizing said at least one computer.

42. The method of claim 41 wherein said step of calculating said geometer further comprises determining a size of said material feature in at least two dimensional units.

43. The method of claim 41 wherein said step of calculating said geometer further comprises determining a size of said material feature in three dimensional units.

44. The method of claim 41 further comprising:
- calculating a fitness for service of said material under evaluation, utilizing said computer.

45. The method of claim 44, further comprising when said material is no longer fit for service then determining remediation of said material utilizing said computer for at least one of redeployment to a new use of said material and an alteration of a shape of said material.

46. The method of claim 41, further comprising evaluating an impact of said material feature upon said material under evaluation, utilizing said computer; and
- when said material is determined not to be fit for service then determining a remediation path utilizing said computer.

47. A method to calculate a material remediation comprising:
- programming a computer to operate a material features acquisition system to detect a plurality of material features;
- recognizing a material feature utilizing said computer; and
- determining a material remediation path, said determination being performed by said computer.

48. The method of claim 47, wherein said material remediation path comprises at least of one of redeployment and alteration to a shape of said material.

49. The method of claim 48, wherein said redeployment comprises providing sensors to monitor utilization of said material.

50. The method of claim 48, wherein said alteration to a shape of said material is an optimal shape for a fitness for service.

51. The method of claim 47, wherein said material remediation path comprises a selection between redeployment to a different use of said material and an alteration of a shape of said material.

* * * * *